United States Patent
Gururajan et al.

(10) Patent No.: US 8,771,648 B2
(45) Date of Patent: Jul. 8, 2014

(54) (TRIMETHOXYPHENYLAMINO) PYRIMIDINYL FORMULATIONS

(75) Inventors: Bindhumadhavan Gururajan, Mölndal (SE); Farhan Abdul Karim Alhusban, Macclesfield (GB); Ian Paul Gabbott, Macclesfield (GB); David Bradley Brook Simpson, Macclesfield (GB); Dawn Sievwright, Macclesfield (GB)

(73) Assignee: Rigel Pharmaceuticals, Inc., South San Francisco, CA (US)

( * ) Notice: Subject to any disclaimer, the term of this patent is extended or adjusted under 35 U.S.C. 154(b) by 0 days.

(21) Appl. No.: 13/559,805

(22) Filed: Jul. 27, 2012

(65) Prior Publication Data

US 2013/0058876 A1 Mar. 7, 2013

Related U.S. Application Data

(60) Provisional application No. 61/512,621, filed on Jul. 28, 2011.

(51) Int. Cl.
A61K 9/00 (2006.01)
A61K 9/46 (2006.01)
A61K 31/542 (2006.01)

(52) U.S. Cl.
USPC ............... 424/43; 424/400; 424/466; 544/51; 514/81

(58) Field of Classification Search
None
See application file for complete search history.

(56) References Cited

U.S. PATENT DOCUMENTS

| | | | |
|---|---|---|---|
| 7,060,827 B2 * | 6/2006 | Singh et al. ............... | 544/323 |
| 7,122,542 B2 | 10/2006 | Singh et al. | |
| 7,329,671 B2 | 2/2008 | Singh et al. | |
| 7,329,672 B2 | 2/2008 | Singh et al. | |
| 7,332,484 B2 * | 2/2008 | Singh et al. ............... | 514/230.5 |
| 7,435,814 B2 | 10/2008 | Singh et al. | |
| 7,449,458 B2 * | 11/2008 | Bhamidipati et al. ..... | 514/230.5 |
| 7,452,879 B2 | 11/2008 | Singh et al. | |
| 7,485,724 B2 | 2/2009 | Singh et al. | |
| 7,498,435 B2 | 3/2009 | Singh et al. | |
| 7,517,886 B2 | 4/2009 | Singh et al. | |
| 7,538,108 B2 | 5/2009 | Singh et al. | |
| 7,550,460 B2 | 6/2009 | Singh et al. | |
| 7,557,210 B2 | 7/2009 | Singh et al. | |
| 7,560,466 B2 | 7/2009 | Singh et al. | |
| 7,563,892 B1 * | 7/2009 | Singh et al. ............... | 544/105 |
| 7,582,648 B2 | 9/2009 | Singh et al. | |
| 7,589,200 B2 | 9/2009 | Singh et al. | |
| 7,642,351 B2 | 1/2010 | Singh et al. | |
| 7,655,797 B2 | 2/2010 | Singh et al. | |
| 7,803,939 B2 | 9/2010 | Singh et al. | |
| 7,812,029 B1 | 10/2010 | Singh et al. | |
| 7,820,819 B2 | 10/2010 | Singh et al. | |
| 7,825,116 B2 | 11/2010 | Singh et al. | |
| 7,884,111 B2 | 2/2011 | Argade et al. | |
| 7,906,644 B2 | 3/2011 | Singh et al. | |
| 7,989,448 B2 | 8/2011 | Singh et al. | |
| 8,148,525 B2 | 4/2012 | Singh et al. | |
| 8,158,621 B2 | 4/2012 | Singh et al. | |
| 8,163,902 B2 | 4/2012 | Bhamidipati et al. | |
| 8,178,671 B2 | 5/2012 | Singh et al. | |
| 8,188,276 B2 | 5/2012 | Singh et al. | |
| 8,211,888 B2 | 7/2012 | Singh et al. | |
| 8,211,889 B2 | 7/2012 | Singh et al. | |
| 8,227,455 B2 | 7/2012 | Masuda et al. | |
| 8,246,984 B2 * | 8/2012 | Parmar ........................ | 424/450 |
| 8,263,122 B2 * | 9/2012 | Sun et al. ...................... | 424/464 |

(Continued)

FOREIGN PATENT DOCUMENTS

| | | |
|---|---|---|
| WO | 2005016893 A2 | 2/2005 |
| WO | 2006078846 A1 | 7/2006 |
| WO | WO 2008064274 A1 * | 5/2008 |
| WO | 2009029682 A1 | 3/2009 |
| WO | 2009061909 A2 | 5/2009 |

OTHER PUBLICATIONS

Javaid et al, 'Dissolution of Aspirin from Tablets Containing Various Buffering Agents', Journal of Pharmaceutcal Sciences, 1972, vol. 61(9), pp. 1370-1373.

(Continued)

*Primary Examiner* — Robert A Wax
*Assistant Examiner* — Olga V Tcherkasskaya
(74) *Attorney, Agent, or Firm* — Travis Young; McDonnell Boehnen Hulbert & Berghoff LLP

(57) ABSTRACT

There are provided pharmaceutical compositions comprising greater than 15% w/w of a compound of Formula (I) as defined herein and/or hydrate thereof and an amount of one or more effervescent agents that is sufficient to provide satisfactory in vitro dissolution; and further comprising one or more pharmaceutically acceptable ingredients; and to processes for obtaining them.

Formula (I)

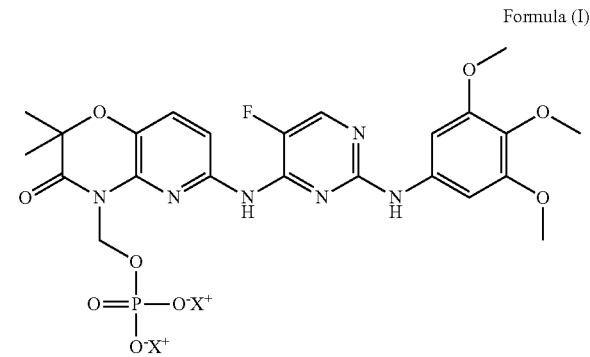

8 Claims, 9 Drawing Sheets

(56) References Cited

U.S. PATENT DOCUMENTS

| | | | |
|---|---|---|---|
| 8,299,242 B2 | 10/2012 | Felfer et al. | |
| 8,372,415 B2* | 2/2013 | Sun et al. | 424/400 |
| 8,389,515 B2 | 3/2013 | Singh et al. | |
| 2005/0113398 A1 | 5/2005 | Argade et al. | |
| 2006/0051406 A1* | 3/2006 | Parmar | 424/450 |
| 2006/0069110 A1* | 3/2006 | Andersen et al. | 514/275 |
| 2006/0211657 A1* | 9/2006 | Singh et al. | 514/81 |
| 2006/0234983 A1* | 10/2006 | Singh et al. | 514/81 |
| 2007/0197782 A1* | 8/2007 | Clough et al. | 544/105 |
| 2007/0293522 A1 | 12/2007 | Singh et al. | |
| 2008/0009484 A1 | 1/2008 | Argade et al. | |
| 2009/0012045 A1* | 1/2009 | Hitoshi et al. | 514/81 |
| 2009/0123539 A1* | 5/2009 | Sun et al. | 424/464 |
| 2009/0156622 A1 | 6/2009 | Singh et al. | |
| 2009/0291129 A1* | 11/2009 | Parmar | 424/450 |
| 2009/0318687 A1 | 12/2009 | Singh et al. | |
| 2011/0003986 A1* | 1/2011 | Felfer et al. | 544/105 |
| 2011/0015155 A1 | 1/2011 | Bhamidipati et al. | |
| 2011/0046126 A1 | 2/2011 | Masuda et al. | |
| 2011/0144059 A1* | 6/2011 | Bhamidipati et al. | 514/81 |
| 2011/0144330 A1 | 6/2011 | Singh et al. | |
| 2011/0190271 A1 | 8/2011 | Argade et al. | |
| 2011/0251177 A1 | 10/2011 | Yu et al. | |
| 2013/0018185 A1 | 1/2013 | Felfer et al. | |
| 2013/0189359 A1 | 7/2013 | Sun et al. | |

OTHER PUBLICATIONS

Khattab et al, 'Effect of Mode of Incorporation of Disintegrants on the Characteristics of Fluid-bed Wet-granulated Tablets', Journal of Pharmacy and Pharmacology, 1992, vol. 45 (8), pp. 687-691.

Sweeny et al, 'Metabolism of Fostamatinib, the Oral Methylene Phosphate Prodrug of the Spleen Tyrosine Kinase Inhibitor R406 in Humans: Contribution of Hepatic and Gut Bacterial Processes to the Overall Biotransformation', Drug Metabolism and Disposition, 2010, vol. 38, pp. 1166-1176.

Braselmann et al, "R406, an Orally Available Spleen Tyrosine Kinase Inhibitor Blocks Fc Receptor Signaling and Reduces Immune Complex-Mediated Inflammation," The Journal of Pharmacology and Experimental Therapeutics, 2006, vol. 319, No. 3, pp. 998-1008.

Baluom et al, "Pharmacokinetics of fostamatinib, a spleen tyrosine kinase (SYK) inhibitior, in healthy human subjects following single and multiple oral dosing in three phase 1 studies," British Journal of Clinical Pharmacology, 2012, 76:1, pp. 78-88.

\* cited by examiner

(TRIMETHOXYPHENYLAMINO) PYRIMIDINYL FORMULATIONS

This application claims the benefit under 35 U.S.C. §119(e) of U.S. Application No. 61/512,621 filed on 28 Jul. 2011.

FIELD OF THE INVENTION

The present invention relates to pharmaceutical/formulation chemistry. The invention is understood to apply generally to formulations of compounds which contain an increased percent loading of the active ingredient. As a preferred aspect, provided herein are formulations of (6-(5-fluoro-2-(3,4,5-trimethoxyphenylamino)pyrimidin-4-ylamino)-2,2-dimethyl-3-oxo-2H-pyrido[3,2-b][1,4]oxazin-4(3H)-yl)methyl phosphate disodium salt (Compound I) which contain an increased percent loading of Compound I. The formulations are useful for treating a variety of diseases including, but not limited to, lymphoma, immune (idiopathic) thrombocytopenia purpura (ITP), and rheumatoid arthritis (RA).

BACKGROUND OF THE INVENTION

In the manufacture of pharmaceutical formulations, it may be desirable for the drug to be administered using the smallest possible number of tablets. Thus it may be desirable for a patient to take the required dose of a drug in a single tablet rather than in more than one tablet, or in two tablets rather than in more than two tablets. Accordingly, it may be desirable for a pharmaceutical formulation to contain an increased percent loading of the active ingredient. However, it is known that increasing the percent loading of active ingredient may lead to a pharmaceutical formulation which exhibits unsatisfactory and/or variable dissolution or to a formulation which exhibits unsatisfactory and/or variable bioavailability. Such formulations may be unsuitable for use by patients.

Compound I (below) is disclosed in international patent application WO2006/078846.

Compound (I)

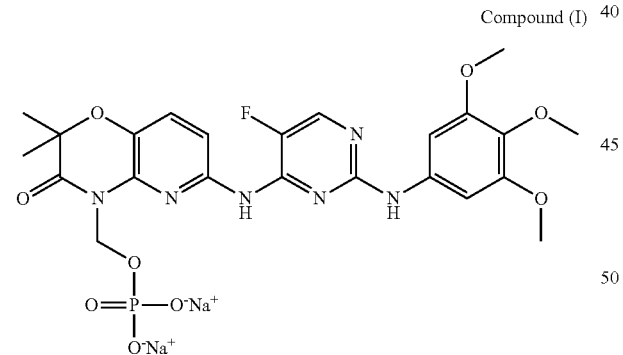

Compound I is a pro-drug of Compound II (below). Compound II is disclosed in international patent application WO2005/016893.

Compound (II)

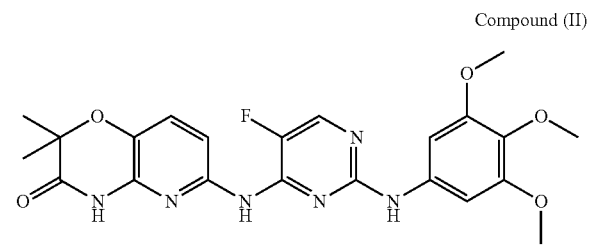 [SMILES: COc1cc(Nc2ncc(F)c(Nc3ccc4c(n3)NC(=O)C(C)(C)O4)n2)cc(OC)c1OC]

Hydrolytically stable pharmaceutical formulations of Compound I which include a water sequestering agent and which are prepared by a wet granulation process are disclosed in international patent application WO2009/061909.

Javaid et al (J. Pharm. Sci. 61 (9) 1972 pp 1370-1373) studied the effect of various classes of buffering agents on the dissolution of aspirin from tablet formulations.

Compound I is currently in clinical studies for the treatment of a variety of diseases such as lymphoma, ITP and RA. Dosing is currently done with orally delivered tablets with a tablet strength of 50 mg. These tablets exhibit satisfactory dissolution at low pH. However, these tablets contain a relatively low percent loading (12.5% w/w) of Compound I.

Tablets with a tablet strength of 100 mg contain an increased percent loading of Compound I. However, these tablets may exhibit unsatisfactory and/or variable dissolution at low pH. Furthermore, these tablets may exhibit unsatisfactory and/or variable bioavailability of the active ingredient.

It is desirable, therefore, to produce new pharmaceutical formulations of Compound I which overcome at least in part the above problems.

DESCRIPTION OF THE INVENTION

This invention is generally directed to formulations of compounds which contain an increased percent loading of the compound of formula (I), in particular to formulations which contain an increased percent loading of active ingredient and exhibit satisfactory dissolution at low pH.

The compound of formula (I) (known hereafter as "Formula (I)") is shown below:

Formula (I)

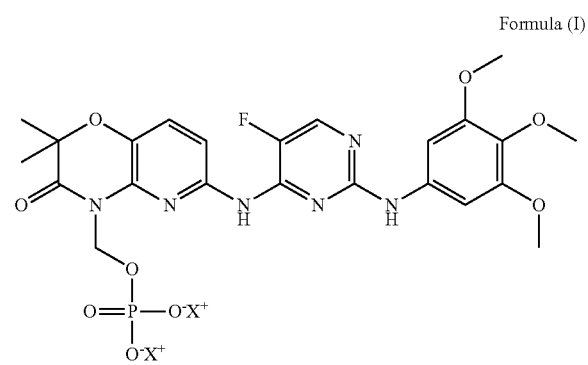

wherein each $X^+$ represents a monovalent cation, for example a monovalent metal cation, such as a sodium cation ($Na^+$), a potassium cation ($K^+$) or a lithium cation ($Li^+$); or wherein $X^+$ and $X^+$ are taken together to represent a divalent cation $X^{2+}$, for example a divalent metal cation, such as a magnesium cation ($Mg^{2+}$), a calcium cation ($Ca^{2+}$) or a barium cation ($Ba^{2+}$);

and/or hydrates thereof (such as the hexahydrate).

For example, Formula (I) may be in the form of Compound (I) above.

In another particular example, Formula (I) may be in the hexahydrate form of Compound (I) (which form is known hereafter as "Formula (II)"). The compound of Formula (II) is shown below.

Formula (II)

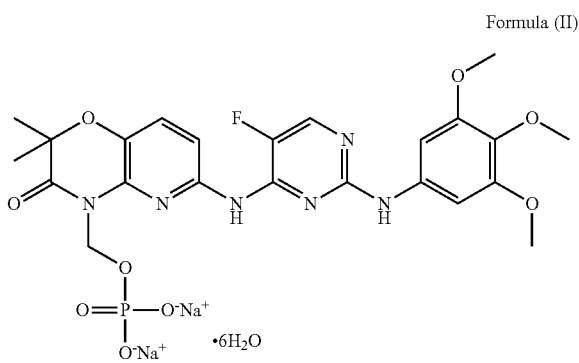

In particular, this invention provides a pharmaceutical composition comprising Formula (I) and/or hydrate thereof and one or more effervescent agents allowing the manufacture of tablets with an increased percent loading of Formula (I) and/or a satisfactory dissolution at low pH.

In a still further aspect, this invention provides a pharmaceutical composition comprising Formula (I) and/or hydrate thereof and sodium hydrogen carbonate allowing the manufacture of tablets with an increased percent loading of Formula (I) and/or a satisfactory dissolution at low pH.

In a yet further aspect, this invention provides a pharmaceutical composition comprising Formula (I) and/or hydrate thereof and potassium hydrogen carbonate allowing the manufacture of tablets with an increased percent loading of Formula (I) and/or a satisfactory dissolution at low pH.

In a still further aspect, this invention provides a pharmaceutical composition comprising Formula (I) and/or hydrate thereof and magnesium carbonate allowing the manufacture of tablets with an increased percent loading of Formula (I) and/or a satisfactory dissolution at low pH.

In a still further aspect, this invention provides a pharmaceutical composition comprising Formula (I) and/or hydrate thereof and sodium carbonate allowing the manufacture of tablets with an increased percent loading of Formula (I) and/or a satisfactory dissolution at low pH.

In a still further aspect, this invention provides a pharmaceutical composition comprising Formula (I) and/or hydrate thereof and calcium carbonate allowing the manufacture of tablets with an increased percent loading of Formula (I) and/or a satisfactory dissolution at low pH.

In a still further aspect, this invention provides a pharmaceutical composition comprising Formula (I) and/or hydrate thereof and potassium carbonate allowing the manufacture of tablets with an increased percent loading of Formula (I) and/or a satisfactory dissolution at low pH.

In a further aspect of the invention, there is provided a pharmaceutical composition comprising greater than 15% w/w of Formula (I) and/or hydrate thereof and an amount of one or more effervescent agents that is sufficient to provide satisfactory in vitro dissolution; and further comprising one or more pharmaceutically acceptable ingredients.

In another aspect of the invention, there is provided a pharmaceutical composition in unit dosage form comprising greater than or equal to 60 mg of Formula (I) and/or hydrate thereof (for example 60 mg, 70 mg, 80 mg, 90 mg, 100 mg, 110 mg, 120 mg, 130 mg, 140 mg, 150 mg, 160 mg, 170 mg, 180 mg, 190 mg or 200 mg) and an amount of one or more effervescent agents that is sufficient to provide satisfactory in vitro dissolution; and further comprising one or more pharmaceutically acceptable ingredients. For the avoidance of doubt, each of the previous integers represents a separate and independent aspect of the invention.

In another aspect of the invention a unit dosage form of the pharmaceutical composition comprises between about 60 mg to about 300 mg of Formula (I) and/or hydrate thereof.

In another aspect of the invention a unit dosage form of the pharmaceutical composition comprises between about 60 mg to about 250 mg of Formula (I) and/or hydrate thereof.

In a still further aspect, a unit dosage form of the pharmaceutical composition comprises between about 100 mg to about 200 mg of Formula (I) and/or hydrate thereof.

In a yet further aspect, a unit dosage form of the pharmaceutical composition comprises between about 125 mg to about 190 mg of Formula (I) and/or hydrate thereof.

In a specific aspect of the invention, a unit dosage form of the pharmaceutical composition comprises 63 mg±3 mg of Formula (I) and/or hydrate thereof.

In a specific aspect of the invention, a unit dosage form of the pharmaceutical composition comprises 126 mg±13 mg of Formula (I) and/or hydrate thereof.

In a further specific aspect of the invention, a unit dosage form of the pharmaceutical composition comprises 190 mg±19 mg of Formula (I) and/or hydrate thereof.

In another aspect of the invention the pharmaceutical composition comprises between about 15% w/w to about 60% w/w of Formula (I) and/or hydrate thereof.

In a further aspect, the pharmaceutical composition comprises between about 20% w/w to about 50% w/w of Formula (I) and/or hydrate thereof.

In a still further aspect, the pharmaceutical composition comprises between about 25% w/w to about 40% w/w of Formula (I) and/or hydrate thereof.

In another aspect of the invention the pharmaceutical composition comprises greater than or equal to 25% w/w of Formula (I) and/or hydrate thereof.

In a specific aspect of the invention, the pharmaceutical composition comprises 25%±2.5% w/w of Formula (I) and/or hydrate thereof.

In a further specific aspect of the invention, the pharmaceutical composition comprises 38%±3.8% of Formula (I) and/or hydrate thereof.

In a still further aspect of the invention, the pharmaceutical composition comprises less than or equal to 30% w/w of one or more effervescent agents.

In a still further aspect of the invention, the pharmaceutical composition comprises less than or equal to 25% w/w of one or more effervescent agents.

In a further aspect, the pharmaceutical composition comprises less than or equal to 20% w/w of one or more effervescent agents.

In a still further aspect, the pharmaceutical composition comprises less than or equal to 15% w/w of one or more effervescent agents.

In a still further aspect, the pharmaceutical composition comprises less than or equal to 10% w/w of one or more effervescent agents.

In a yet further aspect, the pharmaceutical composition comprises greater than or equal to about 5% w/w of one or more effervescent agents, for example between about 5% to 50%, for example between about 5% to 40%, for example between about 5% to 30%, for example between about 5% to 25%, for example between about 5% to 20%, for example between about 5% to 15%, for example between about 5% to 10%. For the avoidance of doubt, each of the previous examples represents a separate and independent aspect of the invention.

In a further aspect of the invention, there is provided a pharmaceutical composition comprising greater than 15% w/w of Formula (I) and/or hydrate thereof and less than or equal to 25% w/w of one or more effervescent agents; and further comprising one or more pharmaceutically acceptable ingredients.

In a further aspect of the invention, there is provided a pharmaceutical composition comprising greater than 15% w/w of Formula (I) and/or hydrate thereof and less than or equal to 20% w/w of one or more effervescent agents; and further comprising one or more pharmaceutically acceptable ingredients.

In a further aspect of the invention, there is provided a pharmaceutical composition comprising greater than 15% w/w of Formula (I) and/or hydrate thereof and less than or equal to 15% w/w of one or more effervescent agents; and further comprising one or more pharmaceutically acceptable ingredients.

In a further aspect of the invention, there is provided a pharmaceutical composition comprising greater than 15% w/w of Formula (I) and/or hydrate thereof and less than or equal to 10% w/w of one or more effervescent agents; and further comprising one or more pharmaceutically acceptable ingredients.

In a further aspect of the invention, there is provided a unit dosage form comprising greater than or equal to 60 mg of Formula (I) and/or hydrate thereof and less than or equal to 110 mg of one or more effervescent agents; and further comprising one or more pharmaceutically acceptable ingredients.

In a further aspect of the invention, there is provided a unit dosage form comprising greater than or equal to 60 mg of Formula (I) and/or hydrate thereof and less than or equal to 75 mg of one or more effervescent agents; and further comprising one or more pharmaceutically acceptable ingredients.

In a still further aspect of the invention, there is provided a unit dosage form comprising greater than or equal to 125 mg of Formula (I) and/or hydrate thereof and less than or equal to 110 mg of one or more effervescent agents; and further comprising one or more pharmaceutically acceptable ingredients.

In a still further aspect of the invention, there is provided a unit dosage form comprising greater than or equal to 125 mg of Formula (I) and/or hydrate thereof and less than or equal to 75 mg of one or more effervescent agents; and further comprising one or more pharmaceutically acceptable ingredients.

In a yet further aspect of the invention, there is provided a unit dosage form comprising greater than or equal to 190 mg of Formula (I) and/or hydrate thereof and less than or equal to 110 mg of one or more effervescent agents; and further comprising one or more pharmaceutically acceptable ingredients.

In a yet further aspect of the invention, there is provided a unit dosage form comprising greater than or equal to 190 mg of Formula (I) and/or hydrate thereof and less than or equal to 75 mg of one or more effervescent agents; and further comprising one or more pharmaceutically acceptable ingredients.

In a yet further aspect of the invention, there is provided a unit dosage form comprising greater than or equal to 225 mg of Formula (I) and/or hydrate thereof and less than or equal to 150 mg of one or more effervescent agents; and further comprising one or more pharmaceutically acceptable ingredients.

In a yet further aspect of the invention, there is provided a unit dosage form comprising greater than or equal to 225 mg of Formula (I) and/or hydrate thereof and less than or equal to 110 mg of one or more effervescent agents; and further comprising one or more pharmaceutically acceptable ingredients.

In a still further embodiment of the invention, the pharmaceutical composition and/or unit dosage form does not comprise an acidifying ingredient (for example does not comprise citric acid). For the avoidance of doubt the term "acidifying ingredient" does not include the compound of Formula (I) or the free acid thereof or hydrate thereof.

In a further aspect of the invention, optional ingredients which can be added to the pharmaceutical composition include one or more of the following:
  a) fillers which, when employed, range between for example about 35 to about 75 weight percent (e.g. about 50 to about 70 weight percent) of the dry formulation;
  b) binding agents which, when employed range between for example about 2 to about 8 weight percent of the dry formulation;
  c) lubricants which, when employed, range from between about 0.25 and 2.0 weight percent of the dry formulation;
  d) disintegrants which, when employed, range from between about 0.5 and 10.0 weight percent (e.g. about 5 weight percent) of the dry formulation; and
  e) water sequestering agents, which, when employed, range from between about 2 weigh percent and 40 weight percent of the dry formulation.

In a further aspect of the invention, the pharmaceutical composition further comprises one or more additional ingredients independently selected from, for example
  a) fillers such as mannitol (e.g. Pearlitol 50c, Peralitol 120c or Pearlitol 160c) or microcrystalline celluloses (e.g. MCC Avicel PH 102, Emcocel 90M, etc.);
  b) binding agents such as Plasdone K29/32, Povidone, microcrystalline celluloses or Kollidon K30;
  c) lubricants such as magnesium stearate;
  d) disintegrants such as sodium starch glycolate, for example ExploTab or Glycolys LV;
  e) Water sequestering agents such as starch (e.g. sodium starch glycolate), magnesium sulfate, calcium chloride, silica, kaolin, microcrystalline celluloses etc.

In another aspect of the invention, there is provided a tablet comprising greater than 15% w/w of Formula (I) and/or hydrate thereof and an amount of one or more effervescent agents that is sufficient to provide satisfactory in vitro dissolution; and further comprising one or more pharmaceutically acceptable ingredients.

In another aspect of the invention, there is provided a tablet comprising greater than or equal to 60 mg of Formula (I) and/or hydrate thereof (for example 60 mg, 70 mg, 80 mg, 90 mg, 100 mg, 110 mg, 120 mg, 130 mg, 140 mg, 150 mg, 160 mg, 170 mg, 180 mg, 190 mg or 200 mg) and an amount of one or more effervescent agents (that is sufficient to provide satisfactory in vitro dissolution; and further comprising one or more pharmaceutically acceptable ingredients. For the avoidance of doubt, each of the previous integers represents a separate and independent aspect of the invention.

In another aspect of the invention, the tablet comprises between about 60 mg to about 300 mg of Formula (I) and/or hydrate thereof.

In another aspect of the invention the tablet comprises between about 60 mg to about 250 mg of Formula (I) and/or hydrate thereof.

In a still further aspect, the tablet comprises between about 100 mg to about 200 mg of Formula (I) and/or hydrate thereof.

In a yet further aspect, the tablet comprises between about 125 mg to about 190 mg of Formula (I) and/or hydrate thereof.

In a specific aspect of the invention, the tablet comprises 63 mg±3 mg of Formula (I) and/or hydrate thereof.

In a specific aspect of the invention, the tablet comprises 126 mg±13 mg of Formula (I) and/or hydrate thereof.

In a further specific aspect of the invention, the tablet comprises 190 mg±19 mg of Formula (I) and/or hydrate thereof.

In another aspect of the invention the tablet comprises between about 15% w/w to about 60% w/w of Formula (I) and/or hydrate thereof.

In a further aspect, the tablet comprises between about 20% w/w to about 50% w/w of Formula (I) and/or hydrate thereof.

In a still further aspect, the tablet comprises between about 25% w/w to about 40% w/w of Formula (I) and/or hydrate thereof.

In another aspect of the invention the tablet comprises greater than or equal to 25% w/w of Formula (I) and/or hydrate thereof.

In a specific aspect of the invention, the tablet comprises 25%±2.5% w/w of Formula (I) and/or hydrate thereof.

In a further specific aspect of the invention, the tablet comprises 38%±3.8% of Formula (I) and/or hydrate thereof.

In a still further aspect of the invention, the tablet comprises less than or equal to 30% w/w of one or more effervescent agents.

In a further aspect, the tablet comprises less than or equal to 20% w/w of one or more effervescent agents.

In a still further aspect, the tablet comprises less than or equal to 15% w/w of one or more effervescent agents.

In a still further aspect, the tablet comprises less than or equal to 10% w/w of one or more effervescent agents.

In a further aspect of the invention, the tablet comprises less than or equal to 75 mg of one or more effervescent agents.

In a yet further aspect, the tablet comprises greater than or equal to about 5% w/w of one or more effervescent agents, for example between about 5% to 50%, for example between about 5% to 40%, for example between about 5% to 30%, for example between about 5% to 25%, for example between about 5% to 20%, for example between about 5% to 15%, for example between about 5% to 10%. For the avoidance of doubt, each of the previous examples represents a separate and independent aspect of the invention.

In a further aspect of the invention, there is provided a tablet comprising greater than 15% w/w of Formula (I) and/or hydrate thereof and less than or equal to 25% w/w of one or more effervescent agents; and further comprising one or more pharmaceutically acceptable ingredients.

In a further aspect of the invention, there is provided a tablet comprising greater than 15% w/w of Formula (I) and/or hydrate thereof and less than or equal to 20% w/w of one or more effervescent agents; and further comprising one or more pharmaceutically acceptable ingredients.

In a further aspect of the invention, there is provided a tablet comprising greater than 15% w/w of Formula (I) and/or hydrate thereof and less than or equal to 15% w/w of one or more effervescent agents; and further comprising one or more pharmaceutically acceptable ingredients.

In a further aspect of the invention, there is provided a tablet comprising greater than 15% w/w of Formula (I) and/or hydrate thereof and less than or equal to 10% w/w of one or more effervescent agents; and further comprising one or more pharmaceutically acceptable ingredients.

In a further aspect of the invention, there is provided a tablet comprising greater than or equal to 60 mg of Formula (I) and/or hydrate thereof and less than or equal to 110 mg of one or more effervescent agents; and further comprising one or more pharmaceutically acceptable ingredients.

In a further aspect of the invention, there is provided a tablet comprising greater than or equal to 60 mg of Formula (I) and/or hydrate thereof and less than or equal to 75 mg of one or more effervescent agents; and further comprising one or more pharmaceutically acceptable ingredients.

In a still further aspect of the invention, there is provided a tablet comprising greater than or equal to 125 mg of Formula (I) and/or hydrate thereof and less than or equal to 110 mg of one or more effervescent agents; and further comprising one or more pharmaceutically acceptable ingredients.

In a still further aspect of the invention, there is provided a tablet comprising greater than or equal to 125 mg of Formula (I) and/or hydrate thereof and less than or equal to 75 mg of one or more effervescent agents; and further comprising one or more pharmaceutically acceptable ingredients.

In a yet further aspect of the invention, there is provided a tablet comprising greater than or equal to 190 mg of Formula (I) and/or hydrate thereof and less than or equal to 110 mg of one or more effervescent agents; and further comprising one or more pharmaceutically acceptable ingredients.

In a yet further aspect of the invention, there is provided a tablet comprising greater than or equal to 190 mg of Formula (I) and/or hydrate thereof and less than or equal to 75 mg of one or more effervescent agents; and further comprising one or more pharmaceutically acceptable ingredients.

In a yet further aspect of the invention, there is provided a tablet comprising greater than or equal to 225 mg of Formula (I) and/or hydrate thereof and less than or equal to 150 mg of one or more effervescent agents; and further comprising one or more pharmaceutically acceptable ingredients.

In a yet further aspect of the invention, there is provided a tablet comprising greater than or equal to 225 mg of Formula (I) and/or hydrate thereof and less than or equal to 110 mg of one or more effervescent agents; and further comprising one or more pharmaceutically acceptable ingredients.

In a still further embodiment of the invention, the tablet does not comprise an acidifying ingredient (for example does not comprise citric acid). For the avoidance of doubt the term "acidifying ingredient" does not include the compound of Formula (I) or the free acid thereof or a hydrate thereof.

The pharmaceutical compositions of this invention may be administered in standard manner for the disease condition that it is desired to treat, for example by oral administration.

These dosage forms will usually include one or more pharmaceutically acceptable excipients which may be selected, for example, from adjuvants, carriers, binders, lubricants, diluents, stabilising agents, buffering agents, emulsifying agents, viscosity-regulating agents, surfactants, preservatives, flavourings or colorants. It will be understood that an individual excipient may be multifunctional. Examples of pharmaceutically acceptable excipients are described in the Handbook of Pharmaceutical Excipients (Fifth Edition, 2005, edited by Ray C. Rowe, Paul J. Sheskey and Sian C. Owen, published by the American Pharmaceutical Association and the Pharmaceutical Press). The active ingredients of the present invention may be administered by oral or parenteral (e.g. intravenous, subcutaneous, intramuscular or intraarticular) administration using conventional systemic dosage forms, such as tablets, capsules, pills, powders, aqueous or oily solutions or suspensions, emulsions and sterile injectable aqueous or oily solutions or suspensions. The active ingredients may also be delivered to the lung and/or airways via oral administration in the form of a solution, suspension, aerosol or dry powder formulation. As will be understood by those skilled in the art, the most appropriate method of administering the active ingredients is dependent on a number of factors.

It will be understood that the therapeutic dose of each active ingredient administered in accordance with the present invention will vary depending upon the particular active ingredient employed, the mode by which the active ingredient is to be administered, and the condition or disorder to be treated.

Buffers, pharmaceutically-acceptable cosolvents such as polyethylene glycol, polypropylene glycol, glycerol or ethanol or complexing agents such as hydroxy-propyl β-cyclodextrin may be used to aid formulation.

In a further aspect of the invention, optional ingredients which can be added to the compositions disclosed herein include one or more of the following:
a) fillers which, when employed, range between for example about 35 to about 75 weight percent (e.g. about 50 to about 70 weight percent) of the dry formulation;
b) binding agents which, when employed range between for example about 2 to about 8 weight percent of the dry formulation;
c) lubricants which, when employed, range from between about 0.25 and 2.0 weight percent of the dry formulation;
d) disintegrants which, when employed, range from between about 0.5 and 10.0 weight percent (e.g. about 5 weight percent) of the dry formulation; and
a) water sequestering agents, which, when employed, range from between about 2 weigh percent and 40 weight percent of the dry formulation;

In a further aspect of the invention, the tablet further comprises one or more additional ingredients independently selected from, for example:
a) fillers such as mannitol (e.g. Pearlitol 50c, Peralitol 120c or Pearlitol 160c) or microcrystalline celluloses (e.g. MCC Avicel PH 102, Emcocel 90M, etc.);
b) binding agents such as Plasdone K29/32, Povidone, microcrystalline celluloses or Kollidon K30;
c) lubricants such as magnesium stearate;
d) disintegrants such as sodium starch glycolate, for example ExploTab or Glycolys LV;
a) Water sequestering agents such as starch (e.g. sodium starch glycolate), calcium chloride, silica, kaolin, microcrystalline celluloses etc.

In a further aspect of the invention, the pharmaceutical composition or unit dosage form comprises the compound of Formula (I) and/or hydrate thereof, one or more effervescent agents and a filler (such as mannitol). In a further aspect of the invention, the pharmaceutical composition or unit dosage form comprises the compound of Formula (I) and/or hydrate thereof, one or more effervescent agents, a filler (such as mannitol) and a binding agent (such as Povidone). In a further aspect of the invention, the pharmaceutical composition or unit dosage form comprises the compound of Formula (I) and/or hydrate thereof, one or more effervescent agents, a filler (such as mannitol), a binding agent (such as Povidone) and a disintegrant (such as sodium starch glycolate). In another aspect the pharmaceutical composition or unit dosage form comprises the compound of Formula (II), one or more effervescent agents, a filler (such as mannitol), a binding agent (such as Povidone), a disintegrant (such as sodium starch glycolate) and a lubricant (such as magnesium stearate).

In a yet further aspect of the invention, the pharmaceutical composition comprises the following components by weight:

| Composition 1 (mg) | |
|---|---|
| Formula (II) | 126 |
| Mannitol | 249 |
| Sodium hydrogen carbonate | 75 |
| Sodium starch glycolate | 25 |
| Povidone | 15 |
| Magnesium stearate | 10 |
| Composition 2 (mg) | |
| Formula (II) | 190 |
| Mannitol | 185 |
| Sodium hydrogen carbonate | 75 |
| Sodium starch glycolate | 25 |
| Povidone | 15 |
| Magnesium stearate | 10 |
| Composition 3 (mg) | |
| Formula (II) | 63 |
| Mannitol | 62 |
| Sodium hydrogen carbonate | 25 |
| Sodium starch 8 glycolate | |
| Povidone | 5 |
| Magnesium stearate | 3 |

In a yet further aspect of the invention, the pharmaceutical composition comprises the following components (% w/w):

| Composition 1 (% w/w) | |
|---|---|
| Formula (II) | 25 |
| Mannitol | 50 |
| Sodium hydrogen carbonate | 15 |
| Sodium starch glycolate | 5 |
| Povidone | 3 |
| Magnesium stearate | 2 |
| Composition 2 and 3 (% w/w) | |
| Formula (II) | 38 |
| Mannitol | 37 |
| Sodium hydrogen carbonate | 15 |
| Sodium starch glycolate | 5 |
| Povidone | 3 |
| Magnesium stearate | 2 |

In a still further aspect, the invention comprises a tablet formed from the pressing of Composition 1 and/or Composition 2 into tablet form. In a still further aspect, the invention comprises a tablet formed from the pressing of Composition 3 into tablet form.

In a separate aspect of the invention, there is provided a process for the preparation of a pharmaceutical composition, as hereinbefore defined, which process comprises bringing into association Formula (I) and/or hydrate thereof with a pharmaceutically acceptable adjuvant, diluents or carrier.

In a further aspect of the invention, there is provided a process for the preparation of a pharmaceutical composition which process comprises mixing Formula (I) and/or hydrate thereof with one or more effervescent agents optionally in the presence of one or more pharmaceutically acceptable ingredients (Step A). In a further aspect, Step A is carried out in the presence of one or more fillers (such as mannitol) and optionally in the presence of one or more pharmaceutically acceptable ingredients. In a still further aspect, Step A is carried out in the presence of one or more fillers (such as mannitol) and optionally in the presence of one or more binding agents and/or one or more disintegrants.

In a further aspect of the invention, there is provided a further process for the preparation of a pharmaceutical composition as defined above which process comprises adding purified water and/or binder solution into the powder mixture from Step A above and mixing to form enlarged granules and optionally passing through a filter screen to break-up large agglomerates (Step B). In a further aspect between about 10% and 45% by weight of purified water is added into the powder mixture.

In a further aspect of the invention, there is provided a further process for the preparation of a pharmaceutical composition which process comprises drying the enlarged granules produced in Step B above until an LOD of less than 10% (e.g. less than 5%) is achieved, to provide dried granules (Step C).

In a further aspect of the invention there is provided a process for the preparation of a pharmaceutical composition which process (wet granulation process) comprises:
 a) blending Formula (I) and/or hydrate thereof with one or more effervescent agents, one or more fillers (such as mannitol) and optionally in the presence of one or more binding agents and/or one or more disintegrants and/or one or more other excipients;
 b) adding between about 10% and 45% by weight of purified water and/or binder solution into the powder mixture of a) above and mixing to form enlarged granules and optionally passing through a filter screen to break-up large agglomerates; and
 c) drying the enlarged granules produced in b) above until an LOD of less than 10% (e.g. less than 5%) is achieved, to provide dried granules.

The dried granules prepared in the methods above are typically between about 25 μm to about 2000 μm in diameter.

In another of its method aspects, this invention further comprises milling the dried granules. In one aspect, the dried granules are milled so that about 90 weight percent have a particle size between about 25 μm to about 2000 μm in diameter.

In yet another aspect, the dried, milled, granules are mixed with a lubricant until homogenous, and then the resulting pharmaceutical composition is tabletted. Suitable lubricants include stearic acid (e.g. magnesium stearate), colloidal silica and talc.

In an alternative aspect of the invention, the lubricant (such as magnesium stearate) can be added to the dry granules prior to milling, and then the resulting pharmaceutical composition is milled and then tabletted.

In another aspect, this invention provides a wet granulation formulation comprising greater than 15% w/w of Formula (I) and/or hydrate thereof and an amount of an effervescent that is sufficient to provide satisfactory in vitro dissolution; and further comprising one or more pharmaceutically acceptable ingredients.

In another aspect of the invention the wet granulation formulation comprises between about 15% w/w to about 60% w/w of Formula (I) and/or hydrate thereof.

In a further aspect, the wet granulation formulation comprises between about 20% w/w to about 50% w/w of Formula (I) and/or hydrate thereof.

In a still further aspect, the wet granulation formulation comprises between about 25% w/w to about 40% w/w of Formula (I) and/or hydrate thereof.

In another aspect of the invention the wet granulation formulation comprises greater than or equal to 25% w/w of Formula (I) and/or hydrate thereof.

In a specific aspect of the invention, the wet granulation formulation contains 25%±2.5% w/w of Formula (I) and/or hydrate thereof.

In a further specific aspect of the invention, the wet granulation formulation contains 38%±3.8% of Formula (I) and/or hydrate thereof.

In a still further aspect of the invention, the wet granulation formulation comprises less than or equal to 30% w/w of one or more effervescent agents.

In a further aspect, the wet granulation formulation comprises less than or equal to 25% w/w of one or more effervescent agents.

In a further aspect, the wet granulation formulation comprises less than or equal to 20% w/w of one or more effervescent agents.

In a still further aspect, the wet granulation formulation comprises less than or equal to 15% w/w of one or more effervescent agents.

In a still further aspect, the wet granulation formulation comprises less than or equal to 10% w/w of one or more effervescent agents.

In a yet further aspect, the wet granulation formulation comprises greater than or equal to about 5% w/w of one or more effervescent agents, for example between about 5% to 50%, for example between about 5% to 40%, for example between about 5% to 30%, for example between about 5% to 25%, for example between about 5% to 20%, for example between about 5% to 15%, for example between about 5% to 10%. For the avoidance of doubt, each of the previous examples represents a separate and independent aspect of the invention.

In a further aspect of the invention, there is provided a wet granulation formulation comprising greater than 15% w/w of Formula (I) and/or hydrate thereof and less than or equal to 25% w/w of one or more effervescent agents; and further comprising one or more pharmaceutically acceptable ingredients.

In a further aspect of the invention, there is provided a wet granulation formulation comprising greater than 15% w/w of Formula (I) and/or hydrate thereof and less than or equal to 20% w/w of one or more effervescent agents; and further comprising one or more pharmaceutically acceptable ingredients.

In a further aspect of the invention, there is provided a wet granulation formulation comprising greater than 15% w/w of Formula (I) and/or hydrate thereof and less than or equal to 15% w/w of one or more effervescent agents; and further comprising one or more pharmaceutically acceptable ingredients.

In a further aspect of the invention, there is provided a wet granulation formulation comprising greater than 15% w/w of Formula (I) and/or hydrate thereof and less than or equal to 10% w/w of one or more effervescent agents; and further comprising one or more pharmaceutically acceptable ingredients.

In another aspect of the invention the wet granulation formulation comprises Formula (I) and/or hydrate thereof, water, one or more effervescent agents, filler(s), binding agent(s) and disintegrant(s).

In a still further embodiment of the invention, the wet granulation formulation does not comprise an acidifying ingredient (for example does not comprise citric acid). For the avoidance of doubt the term "acidifying ingredient" does not include the compound of Formula (I) or the free acid thereof or a hydrate thereof.

In another aspect, this invention provides a tablet formed by compressing the wet granulation formulation.

In a further aspect of the invention, there is provided a further process for the preparation of a pharmaceutical composition as defined above which process comprises passing the mixture of Step A above through a compactor to produce dry granules (Step D).

In a further aspect of the present invention there is provided a process for the manufacture of a pharmaceutical composition which process (roller compaction process) comprises:
(a) blending Formula (I) and/or hydrate thereof with one or more effervescent agents, one or more fillers (such as mannitol) and optionally in the presence of one or more binding agents and/or one or more disintegrants and/or one or more other excipients;
(b) passing the mixture of (a) above through a compactor to produce dry granules.

The dried granules prepared in the methods above are typically between about 25 μm to about 2000 μm in diameter.

In another of its method aspects, this invention further comprises milling the dried granules. In one aspect, the dried granules are milled so that about 90 weight percent have a particle size between about 25 μm to about 2000 μm in diameter.

In another aspect, a lubricant is added to the mixture of (a) above prior to passing through a compactor. Suitable lubricants include stearic acid (e.g. magnesium stearate), colloidal silica and talc.

In yet another aspect, the resulting pharmaceutical composition is tabletted. In an alternative aspect of the invention, the lubricant (such as magnesium stearate) can be added to the dry granules prior to milling, and then the resulting pharmaceutical composition is milled and then tabletted.

In another aspect, this invention provides a roller compaction formulation comprising greater than 15% w/w of Formula (I) and/or hydrate thereof and an amount of one or more effervescent agents that is sufficient to provide satisfactory in vitro dissolution; and further comprising one or more pharmaceutically acceptable ingredients.

In another aspect of the invention the roller compaction formulation comprises between about 15% w/w to about 60% w/w of Formula (I) and/or hydrate thereof.

In a further aspect, the roller compaction formulation comprises between about 20% w/w to about 50% w/w of Formula (I) and/or hydrate thereof.

In a still further aspect, the roller compaction formulation comprises between about 25% w/w to about 40% w/w of Formula (I) and/or hydrate thereof.

In another aspect of the invention the roller compaction formulation comprises greater than or equal to 25% w/w of Formula (I) and/or hydrate thereof.

In a specific aspect of the invention, the roller compaction formulation contains 25%±2.5% w/w of Formula (I) and/or hydrate thereof.

In a further specific aspect of the invention, the roller compaction formulation contains 38%±3.8% of Formula (I) and/or hydrate thereof.

In a still further aspect of the invention, the roller compaction formulation comprises less than or equal to 30% w/w of one or more effervescent agents.

In a further aspect, the roller compaction formulation comprises less than or equal to 20% w/w of one or more effervescent agents.

In a still further aspect, the roller compaction formulation comprises less than or equal to 15% w/w of one or more effervescent agents.

In a still further aspect, the roller compaction formulation comprises less than or equal to 10% w/w of one or more effervescent agents.

In a yet further aspect, the roller compaction formulation comprises greater than or equal to about 5% w/w of one or more effervescent agents, for example between about 5% to 50%, for example between about 5% to 40%, for example between about 5% to 30%, for example between about 5% to 25%, for example between about 5% to 20%, for example between about 5% to 15%, for example between about 5% to 10%. For the avoidance of doubt, each of the previous examples represents a separate and independent aspect of the invention.

In a further aspect of the invention, there is provided a roller compaction formulation comprising greater than 15% w/w of Formula (I) and/or hydrate thereof and less than or equal to 25% w/w of one or more effervescent agents; and further comprising one or more pharmaceutically acceptable ingredients.

In a further aspect of the invention, there is provided a roller compaction formulation comprising greater than 15% w/w of Formula (I) and/or hydrate thereof and less than or equal to 20% w/w of one or more effervescent agents; and further comprising one or more pharmaceutically acceptable ingredients.

In a further aspect of the invention, there is provided a roller compaction formulation comprising greater than 15% w/w of Formula (I) and/or hydrate thereof and less than or equal to 15% w/w of one or more effervescent agents; and further comprising one or more pharmaceutically acceptable ingredients.

In a further aspect of the invention, there is provided a roller compaction formulation comprising greater than 15% w/w of Formula (I) and/or hydrate thereof and less than or equal to 10% w/w of an effervescent; and further comprising one or more pharmaceutically acceptable ingredients.

In another aspect of the invention the roller compaction formulation comprises Formula (I) and/or hydrate thereof, one or more effervescent agents, filler(s), binding agent(s), lubricant(s) and disintegrant(s).

In a still further embodiment of the invention, the roller compaction formulation does not comprise an acidifying ingredient (for example does not comprise citric acid). For the avoidance of doubt the term "acidifying ingredient" does not include the compound of Formula (I) or the free acid thereof or a hydrate thereof.

In another aspect, this invention provides a tablet formed by compressing the roller compaction formulation.

In a further aspect of the invention there is provided a process for the manufacture of a pharmaceutical composition which process (direct compression process) comprises:
(a) blending Formula (I) and/or hydrate thereof with one or more effervescent agents, one or more fillers (such as mannitol) and optionally in the presence of one or more binding agents and/or one or more disintegrants and/or one or more lubricants and/or one or more other excipients;
(b) compressing the mixture of (a) above.

In another aspect of the invention the direct compression formulation comprises Formula (I) and/or hydrate thereof, one or more effervescent agents, filler(s), binding agent(s), lubricant(s) and disintegrant(s).

In another aspect, this invention provides a tablet formed directly by compressing the mixture of (a) above.

In another aspect, this invention provides a direct compression formulation comprising greater than 15% w/w of Formula (I) and/or hydrate thereof and an amount of one or more effervescent agents that is sufficient to provide satisfactory in vitro dissolution; and further comprising one or more pharmaceutically acceptable ingredients.

In another aspect of the invention the direct compression formulation comprises between about 15% w/w to about 60% w/w of Formula (I) and/or hydrate thereof.

In a further aspect, the direct compression formulation comprises between about 20% w/w to about 50% w/w of Formula (I) and/or hydrate thereof.

In a still further aspect, the direct compression formulation comprises between about 25% w/w to about 40% w/w of Formula (I) and/or hydrate thereof.

In another aspect of the invention the direct compression formulation comprises greater than or equal to 25% w/w of Formula (I) and/or hydrate thereof.

In a specific aspect of the invention, the direct compression formulation contains 25%±2.5% w/w of Formula (I) and/or hydrate thereof.

In a further specific aspect of the invention, the direct compression formulation contains 38%±3.8% of Formula (I) and/or hydrate thereof.

In a still further aspect of the invention, the direct compression formulation comprises less than or equal to 30% w/w of one or more effervescent agents.

In a further aspect, the direct compression formulation comprises less than or equal to 20% w/w of one or more effervescent agents.

In a still further aspect, the direct compression formulation comprises less than or equal to 15% w/w of one or more effervescent agents.

In a still further aspect, the direct compression formulation comprises less than or equal to 10% w/w of one or more effervescent agents.

In a yet further aspect, the direct compression formulation comprises greater than or equal to about 5% w/w of one or more effervescent agents, for example between about 5% to 50%, for example between about 5% to 40%, for example between about 5% to 30%, for example between about 5% to 25%, for example between about 5% to 20%, for example between about 5% to 15%, for example between about 5% to 10%. For the avoidance of doubt, each of the previous examples represents a separate and independent aspect of the invention.

In a further aspect of the invention, there is provided a direct compression formulation comprising greater than 15% w/w of Formula (I) and/or hydrate thereof and less than or equal to 25% w/w of one or more effervescent agents; and further comprising one or more pharmaceutically acceptable ingredients.

In a further aspect of the invention, there is provided a direct compression formulation comprising greater than 15% w/w of Formula (I) and/or hydrate thereof and less than or equal to 20% w/w of one or more effervescent agents; and further comprising one or more pharmaceutically acceptable ingredients.

In a further aspect of the invention, there is provided a direct compression formulation comprising greater than 15% w/w of Formula (I) and/or hydrate thereof and less than or equal to 15% w/w of one or more effervescent agents; and further comprising one or more pharmaceutically acceptable ingredients.

In a further aspect of the invention, there is provided a direct compression formulation comprising greater than 15% w/w of Formula (I) and/or hydrate thereof and less than or equal to 10% w/w of one or more effervescent agents; and further comprising one or more pharmaceutically acceptable ingredients.

In a still further embodiment of the invention, the direct compression formulation does not comprise an acidifying ingredient (for example does not comprise citric acid). For the avoidance of doubt the term "acidifying ingredient" does not include the compound of Formula (I) or the free acid thereof or a hydrate thereof.

The pharmaceutical composition and/or tablet and/or wet granulation formulation and/or roller compaction formulation and/or direct compression formulation can additionally and optionally include a colourant, as long as it is approved and certified by the FDA. For example, exemplary colours include allura red, acid fuschin D, napthalone red B, food orange 8, eosin Y, phloxine B, erythrosine, natural red 4, carmine, red iron oxide, yellow iron oxide, black iron oxide, titanium dioxide and the like.

Sweetening agents can also be added to the pharmaceutical composition and/or tablet and/or wet granulation formulation and/or roller compaction formulation and/or direct compression formulation or to the outer core of the tablet to create or add to the sweetness. Saccharide fillers and binders, e.g. mannitol, lactose, and the like, can add to this effect. For example, cyclamates, saccharin, aspartame, acesulfame K (Mukherjee (1997) Food Chem. Toxicol. 35:1177-1179), or the like (Rolls (1991) Am. J. Clin. Nutr. 53:872-878), can be used. Sweeteners other than sugars have the advantage of reducing the bulk volume of the pharmaceutical composition and/or tablet (core tablet and/or coat) and/or wet granulation formulation and/or roller compaction formulation and/or direct compression formulation and not affecting the physical properties of the tablet.

It will be understood by the skilled person that the incorporation of one or more effervescent agents into the pharmaceutical composition may necessitate the use of appropriate packaging. In a further aspect of the invention, there is provided packaging suitable for a pharmaceutical composition wherein the pharmaceutical composition comprises one or more effervescent agents. Examples of such packaging include packaging providing moisture protection. Examples of such packaging include for example PVC packaging, PVC/PVDC packaging, PVC/CTFE packaging, OPA/aluminium/PVC packaging, aluminium packaging or aluminium blister packaging. Further examples of such packaging include bottles with or without desiccants.

Compounds of the invention can be used to treat or prevent autoimmune diseases and/or symptoms of such diseases and are expected to be useful as a therapeutic and prophylactic agent for diseases associated with an abnormal immune response (e.g. autoimmune diseases and allergic diseases) and various infections and cancers which are required for activation of an immune response. For example, compounds of the invention may be administered to a mammal, including man, for the treatment of the following non-limiting examples of autoimmune conditions or diseases: rheumatoid arthritis, irritable bowel syndrome, systemic lupus erythematosus, multiple sclerosis, Hashimoto's thyroiditis, Graves' disease, Addison's disease, diabetes mellitus, idiopathic thrombocytopaenic purpura, eosinophilic fasciitis, hyper-IgE syndrome, antiphospholipid syndrome and Sazary syndrome. Compounds of the invention may be administered to a mammal, including man, for the treatment of the following non-limiting examples of cancers: treatment of common cancers including prostate, breast, lung, ovarian, pancreatic, bowel and colon, stomach, skin and brain tumours and malignancies affecting the bone marrow (including the leukaemias) and lymphoproliferative systems, such as Hodgkin's and non-Hodgkin's lymphoma; including the prevention and treatment of metastatic disease and tumour recurrences, and paraneoplastic syndromes.

According to a further feature of the present invention there is provided a method for treating an autoimmune disease state in a mammal, such as man, suffering from, or at risk of, said disease state, which comprises administering to a mammal in need of such treatment a therapeutically effective amount of a compound of Formula (I) and/or a hydrate thereof.

The invention also provides a compound of Formula (I) and/or a hydrate thereof, for use in therapy.

In another aspect the invention provides the use of a compound of Formula (I) and/or a hydrate thereof in the manufacture of a medicament for use in therapy.

In a further aspect, there is provided a method for treating rheumatoid arthritis in a mammal, such as man, suffering from, or at risk of, said disease state, which comprises administering to a mammal in need of such treatment a therapeutically effective amount of a compound of Formula (I) and/or a hydrate thereof.

The invention also provides a compound of Formula (I) and/or a hydrate thereof, for use in the treatment of rheumatoid arthritis.

In another aspect the invention provides the use of a compound of Formula (I) and/or a hydrate thereof in the manufacture of a medicament for use in the treatment of rheumatoid arthritis.

In a further aspect, there is provided a method for treating systemic lupus erythematosus in a mammal, such as man, suffering from, or at risk of, said disease state, which comprises administering to a mammal in need of such treatment a therapeutically effective amount of a compound of Formula (I) and/or a hydrate thereof.

The invention also provides a compound of Formula (I) and/or a hydrate thereof, for use in the treatment of systemic lupus erythematosus.

In another aspect the invention provides the use of a compound of Formula (I) and/or a hydrate thereof in the manufacture of a medicament for use in the treatment of systemic lupus erythematosus.

In a further aspect, there is provided a method for treating cancer in a mammal, such as man, suffering from, or at risk of, said disease state, which comprises administering to a mammal in need of such treatment a therapeutically effective amount of a compound of Formula (I) and/or a hydrate thereof.

The invention also provides a compound of Formula (I) and/or a hydrate thereof, for use in the treatment of cancer.

In another aspect the invention provides the use of a compound of Formula (I) and/or a hydrate thereof in the manufacture of a medicament for use in the treatment of cancer.

Definitions

As used herein, the term "effervescent agent" refers to any pharmaceutically acceptable material which evolves a gas when placed in an aqueous environment, for example the evolution of carbon dioxide on acidification. An example of an effervescent agent is a carbonate, for example a metal carbonate (such as sodium carbonate, potassium carbonate, magnesium carbonate, calcium carbonate or aluminium carbonate) or an organic carbonate (such as disodium glycine carbonate, dimethyl carbonate or ethylene carbonate). A further example of an effervescent agent is a bicarbonate, for example a metal bicarbonate (such as sodium hydrogen carbonate or potassium hydrogen carbonate). For the avoidance of doubt, each of the effervescent agents referred to above represents a separate and independent aspect of the invention.

In one particular aspect of the invention, the effervescent agent is selected from a carbonate or bicarbonate. In another particular aspect of the invention, the effervescent agent is selected from a metal carbonate or a metal bicarbonate. In another particular aspect of the invention, the effervescent agent is selected from sodium hydrogen carbonate, potassium hydrogen carbonate, magnesium carbonate or sodium carbonate. In a further particular aspect of the invention, the effervescent agent is sodium hydrogen carbonate.

For the avoidance of doubt, reference to either a % w/w or to a weight (in mgs) of "one or more effervescent agents" in any aspect of the invention refers to the combined total % w/w or the combined total weight (in mgs) of all effervescent agents. By way of example, a pharmaceutical composition comprising 10% w/w of sodium hydrogen carbonate and 10% w/w magnesium carbonate would comprise 20% w/w of "one or more effervescent agents".

As used herein, the term "binding agent" refers to a pharmaceutically acceptable compound or composition added to a formulation to hold the active pharmaceutical ingredient and inactive ingredients together in a cohesive mix. Dry binders used for direct compaction must exhibit cohesive and adhesive forces so that when compacted the particles agglomerate. Binders used for wet granulation are hydrophilic and soluble in water and are usually dissolved in water to form a wet mass that is then granulated. Examples of suitable binding agents includes, but are not limited to, Povidone, Plasdone K29/32, Plasdone S-630, hydropropyl cellulose, methylcellulose, polyvinylpyrrolidone, aluminium stearate, hydroxypropylmethylcellulose and the like. It is possible for such binding agents to additionally act as water sequestering agents (e.g. Povidone).

As used herein, the term "filler" refers to any pharmaceutically acceptable material or composition added to a formulation to add bulk. Suitable fillers include, but are not limited to, mannitol, lactose, microcrystalline cellulose, silified microcrystalline cellulose and dicalcium phosphate.

As used herein, the term "lubricant" refers to any pharmaceutically acceptable agent which reduces surface friction, lubricates the surface of the granule, decreases tendency to build-up of static electricity, and/or reduces friability of the granules. Thus, lubricants can serve as anti-agglomeration agents. Examples of suitable lubricants are magnesium stearate, stearic acid, sodium stearyl fumarate, colloidal silica, talc, other hydrogenated vegetable oil or triglycerides.

As used herein, the term "disintegrant" refers to materials added to the composition to help it break apart (disintegrate) and release the medicaments. Examples of disintegrants include, but are not limited to, non-saccharide water soluble polymers, such as cross-linked povidine. Other disintegrants that can also be used include, e.g. croscarmellose sodium, sodium starch glycolate, and the like, e.g. see Khattab (1992) J. Pharm. Pharmacol. 45:687-691.

The term "drying" and "dried" refer to a process which decreases the water content of a composition to a desired level.

The terms "compressing", "molding" and "pressing" refer to the process of applying compressive force to a formulation (powder or granules), as within a die, to form a tablet. The terms "compressed tablet" and "pressed tablet" mean any tablet formed by such a process.

The term "tablet" is used in its common context, and refers to a solid composition made by compressing and/or molding a mixture of compositions in a form convenient for swallowing or application to any body cavity.

As used herein, "tablet strength" is the equivalent mass of the free acid form of Compound I based on the amount of Formula (II) present in the tablet. Thus by way of example, a tablet strength of 50 mg will contain about 63 mg of Formula (II).

As used herein, "percent loading" is calculated by reference to the amount of Formula (II).

The term "low pH" refers to a measured pH of less than 5, such as less than 3, for example between 0 and 3.

The term "satisfactory in vitro dissolution" refers to a percent dissolution of greater than or equal to 70% within 30 minutes in 0.1N hydrochloric acid solution at 37° C.+0.5° C. as measured using the general procedure of the United States Pharmacopeia (Apparatus 2).

Dissolution Performance of the Existing Tablet

Reference Table 1 shows the composition of the tablet of Formula (II) with a tablet strength of 50 mg (the 50 mg tablet) as currently administered in ongoing clinical trials together with an equivalent tablet of Formula (II) with a tablet strength of 100 mg (the 100 mg tablet). The tablets were prepared in accordance with WO2009/061909.

Tablet strength is the equivalent mass of the free acid form of Compound I based on the amount of Formula (II) present in the tablet. Thus by way of example, a tablet strength of 50 mg will contain about 63 mg of Formula (II). The percent loading of Formula (II) in the 50 mg tablet is 12.5% whereas the percent loading of Formula (II) in the 100 mg tablet is 25%.

REFERENCE TABLE 1

| Material | 50 mg tablet (% w/w) | 100 mg tablet (% w/w) |
|---|---|---|
| Formula (II) | 12.5 | 25.0 |
| Pregelatinised starch | 37.02 | 30.77 |
| Sodium starch glycolate | 5.77 | 5.77 |
| Microcrystalline cellulose | 37.02 | 30.77 |
| Povidone | 2.88 | 2.88 |
| Magnesium stearate | 0.96 | 0.96 |
| Opadry II Blue 85F99003 | 3.85 | 3.85 |

Dissolution was determined according to the general procedure of the United States Pharmacopeia using Apparatus 2 with 900 mL of 0.1N hydrochloric acid solution at 37° C.±0.5° C. and stirrer speed of 75 rpm. At 5, 15, 30, 45 and 60 minutes, 10 mL of dissolution solution was withdrawn and filtered through a 0.45 µM PTFE filter. The concentration of Formula (II) in solution was determined by uv spectroscopy (e.g. Agilent 8453) at a wavelength of 324 nm and path length of 2 mm against an external standard solution.

Table 2 shows the resulting tablet percent dissolution in 0.1N hydrochloric acid for the 50 mg reference tablet and for three separate batches of the 100 mg tablet having the reference formulation set forth in Table 1 after 30 minutes. A plot showing the dissolution profile over time is shown in FIG. 1.

TABLE 2

| Formulation Strength (mg) | Formula (II) (% w/w) | Mean % dissolution in 0.1N HCl at 30 minutes |
|---|---|---|
| 50 | 12.5 | 87 |
| 100 - A | 25 | 65 |
| 100 - B | 25 | 41 |
| 100 - C | 25 | 16 |

The 100 mg tablet exhibits unsatisfactory and/or variable dissolution performance (varying between 16% and 65%). This compares to the 50 mg tablet which exhibits satisfactory dissolution.

We have investigated a number of formulations where the percent loading of Formula (II) is 25% or greater, in a desire to increase the mean percent dissolution performance of a tablet which contains an increased percent loading of Formula (II). Mannitol, microcrystalline cellulose, silified microcrystalline cellulose, sodium chloride and di-sodium hydrogen phosphate, and individual combinations thereof, all failed to provide a percent dissolution in 0.1N hydrochloric acid after 30 minutes of greater than 50%. In addition, formulations which comprised citric acid, arginine, meglumine and Polyplasdone Crospovidine or combinations thereof also failed to provide satisfactory dissolution.

It was therefore surprising to find that formulations which contained an effervescent agent exhibited satisfactory dissolution, even where said formulations contained an increased percent loading of Formula (II) (e.g. 25% and/or 37.5%, and up to 50%).

Table 3 shows the selection of components for sixteen separate experiments to investigate dissolution in a tablet with an increased percent loading of Formula (II). The results are shown in FIG. 2. Table 4 shows the selection of components for a further eight experiments and the results for these are shown in FIG. 3. Tables 10 and 11 (in Example 6) show the selection of components for a further twelve experiments and the results for these are shown in FIG. 6. In each case, all experiments which did not use an effervescent agent failed to achieve a percent dissolution in 0.1N hydrochloric acid after 30 minutes of greater than 50%. However, experiments which used an effervescent agent showed satisfactory dissolution. For the avoidance of doubt, the reference to water in Tables 3 and 4 refers to the amount of water added during the processing of the formulation and prior to any subsequent drying step. The composition of any final tablet form will not include the level of water indicated.

TABLE 3

| Run | Formula (II) (% w/w) | Filler 1 | Filler 2 | Disintegrant (5% w/w) | SLS (% w/w) | MgSt (% w/w) | Water (% w/w) |
|---|---|---|---|---|---|---|---|
| 1 | 25.0 | Mannitol | Sodium Bicarbonate | SSG | 0 | 1 | 15 |
| 2 | 25.0 | Mannitol | MCC | CCS | 0 | 1 | 35 |
| 3 | 37.5 | SMCC | Sodium Bicarbonate | SSG | 0 | 1 | 25 |
| 4 | 37.5 | Mannitol | Sodium Bicarbonate | SSG | 5 | 1 | 15 |
| 5 | 37.5 | SMCC | MCC | CCS | 0 | 1 | 55 |
| 6 | 37.5 | SMCC | MCC | SSG | 5 | 1 | 55 |
| 7 | 25.0 | SMCC | MCC | CCS | 5 | 1 | 55 |
| 8 | 25.0 | Mannitol | MCC | SSG | 5 | 1 | 35 |
| 9 | 25.0 | SMCC | Sodium Bicarbonate | CCS | 0 | 1 | 40 |

TABLE 3-continued

| Run | Formula (II) (% w/w) | Filler 1 | Filler 2 | Disintegrant (5% w/w) | SLS (% w/w) | MgSt (% w/w) | Water (% w/w) |
|---|---|---|---|---|---|---|---|
| 10 | 37.5 | Mannitol | Sodium Bicarbonate | CCS | 0 | 1 | 25 |
| 11 | 25.0 | SMCC | MCC | SSG | 0 | 1 | 55 |
| 12 | 37.5 | Mannitol | MCC | SSG | 0 | 1 | 30 |
| 13 | 37.5 | SMCC | Sodium Bicarbonate | CCS | 5 | 1 | 30 |
| 14 | 25.0 | SMCC | Sodium Bicarbonate | SSG | 5 | 1 | 30 |
| 15 | 37.5 | Mannitol | MCC | CCS | 5 | 1 | 35 |
| 16 | 25.0 | Mannitol | Sodium Bicarbonate | CCS | 5 | 1 | 15 |

TABLE 4

| Run | Cmpd I (% w/w) | MCC (% w/w) | Filler 1 | Filler 1 (% w/w) | PVP (% w/w) | SSG (% w/w) | MgSt (% w/w) | Mannitol (% w/w) | Water (% w/w) |
|---|---|---|---|---|---|---|---|---|---|
| 1 | 37.9 | 15 | disodium hydrogen phosphate | 30 | 3 | 5 | 1.5 | 7.1 | 22.5 |
| 2 | 37.9 | 0 | disodium hydrogen phosphate | 10 | 3 | 5 | 1.5 | 42.1 | 20 |
| 3 | 37.9 | 0 | sodium hydrogen carbonate | 30 | 3 | 5 | 1.5 | 22.1 | 15 |
| 4 | 25.2 | 0 | disodium hydrogen phosphate | 10 | 3 | 5 | 1.5 | 54.8 | 17.5 |
| 5 | 25.2 | 0 | disodium hydrogen phosphate | 30 | 3 | 5 | 1.5 | 34.8 | 25 |
| 6 | 25.2 | 15 | disodium hydrogen phosphate | 10 | 3 | 5 | 1.5 | 39.8 | 25 |
| 7 | 25.2 | 15 | sodium hydrogen carbonate | 30 | 3 | 5 | 1.5 | 19.8 | 18.3 |
| 8 | 37.9 | 15 | sodium hydrogen carbonate | 10 | 3 | 5 | 1.5 | 27.1 | 26.7 |

Whilst we do not wish to be limited by theoretical considerations, the addition of an effervescent agent (such as sodium hydrogen carbonate) appears to change the disintegration mechanism from a swelling disintegration mechanism, wherein high drug loading prevents rapid hydration/swelling events and consequently leads to slower disintegrating tablets which only dissolves slowly, to an erosion dissolution mechanism. In particular, it is thought that incorporation of an effervescent agent (such as sodium hydrogen carbonate) allows the tablet to rapidly disintegrate (break) into small particles which dissolve quickly.

Manufacturing Process

The particular manufacturing process of this invention for wet granulation formulations comprises premixing all of the required formulation components except water and lubricant(s). In one preferred aspect, premixing is conducted in a mixer-granulator such as a PMA25, and premixing comprises mixing the components together at impeller speeds ranging between about 50 to about 500 rpm for a period of between about 2 to about 20 minutes. In another preferred aspect, batches were dry-blended for 4 minutes at 440 rpm with a chopper speed of 1500 rpm using a Diosna granulator P1/6.

Water is then sprayed onto/into the dry composition to form a wet granulation formulation described herein. The water is added at for example a constant rate over a period of for example from about 0.05 kg/min to about 1.0 kg/min with either constant mixing during addition or mixing after addition. In either event, mixing is continued until the wet granulation composition is homogenous. In an alternative aspect, water is added at a rate of 15 mL/min to a total volume of 8-12% (w/w).

The wet granulation formulation is then dried using conventional techniques to reduce water to a predetermined level. In one aspect, the water content of the dried granulated formulation is less than about 10% (for example about 5%) by weight. Drying can be conducted at various temperatures and times. One skilled in the art could readily determine the appropriate drying times based on the initial water content, the desired final water content, and the drying temperature(s) employed.

The particular manufacturing process of this invention for roller compaction formulations comprises preblending all of the required formulation components until homogenous. In one preferred aspect, preblending is conducted in a blender-granulator such as a Copley Mobile Blender, and preblending comprises mixing the components together at speeds ranging between about 50 to about 500 rpm for a period of between about 2 to about 20 minutes.

The homogenous mix is then passed through a roller compactor, such as an Alexanderwerk WP120 to produce dry granules.

The dried granulated formulation produced via the wet granulation and/or roller compaction process is milled using conventional techniques and machinery. In one aspect, the formulation is milled through an appropriate mesh screen using commercially available milling equipment such as, e.g. Quadro Comil.

Following milling, the lubricant(s) (for example magnesium stearate) is added to the granulated formulation which is then blended using conventional techniques and machinery. Alternatively, the lubricant(s) (such as magnesium stearate) can be added to the dry granules prior to milling.

The pressing or compressing of the dried, granulated, milled and blended formulation can be accomplished using any tablet press. Many alternative means to effect this step are available, and the invention is not limited by the use of any particular equipment. In one aspect, the compression step is carried out using a Piccola Riva PV tablet press. In another aspect, the compression step is carried out by using an F3 Manesty press.

The diameter and shape of the tablet depends upon the die and punches selected for the compression of the milled and mixed formulation. Tablets can be discoid, oval, oblong, round, cylindrical, triangular, and the like. The tablets may be scored to facilitate breaking. The top or lower surface can be embossed or debossed with symbols or letters.

The compression force can be selected based on the type/model of press, a desired hardness of the resulting tabets, as well as other attributes such as friability, disintegration or dissolution characteristics, etc.

The particular manufacturing process of this invention for direct compression formulations comprises preblending all of the required formulation components. In one preferred aspect, all of the required formulation components except lubricant(s) are mixed in a mixer-granulator (such as a PMA25 at impeller speeds ranging between about 50 to about 500 rpm for a period of between about 2 to about 20 minutes), and thereafter lubricant(s) added and the resulting mixture blended (using for example a WAB turbula at speeds ranging between about 50 to about 500 rpm for a period of between about 2 to about 20 minutes). The resulting mixture is then compressed into tablet core using conventional techniques.

EXAMPLES

Figure 1:
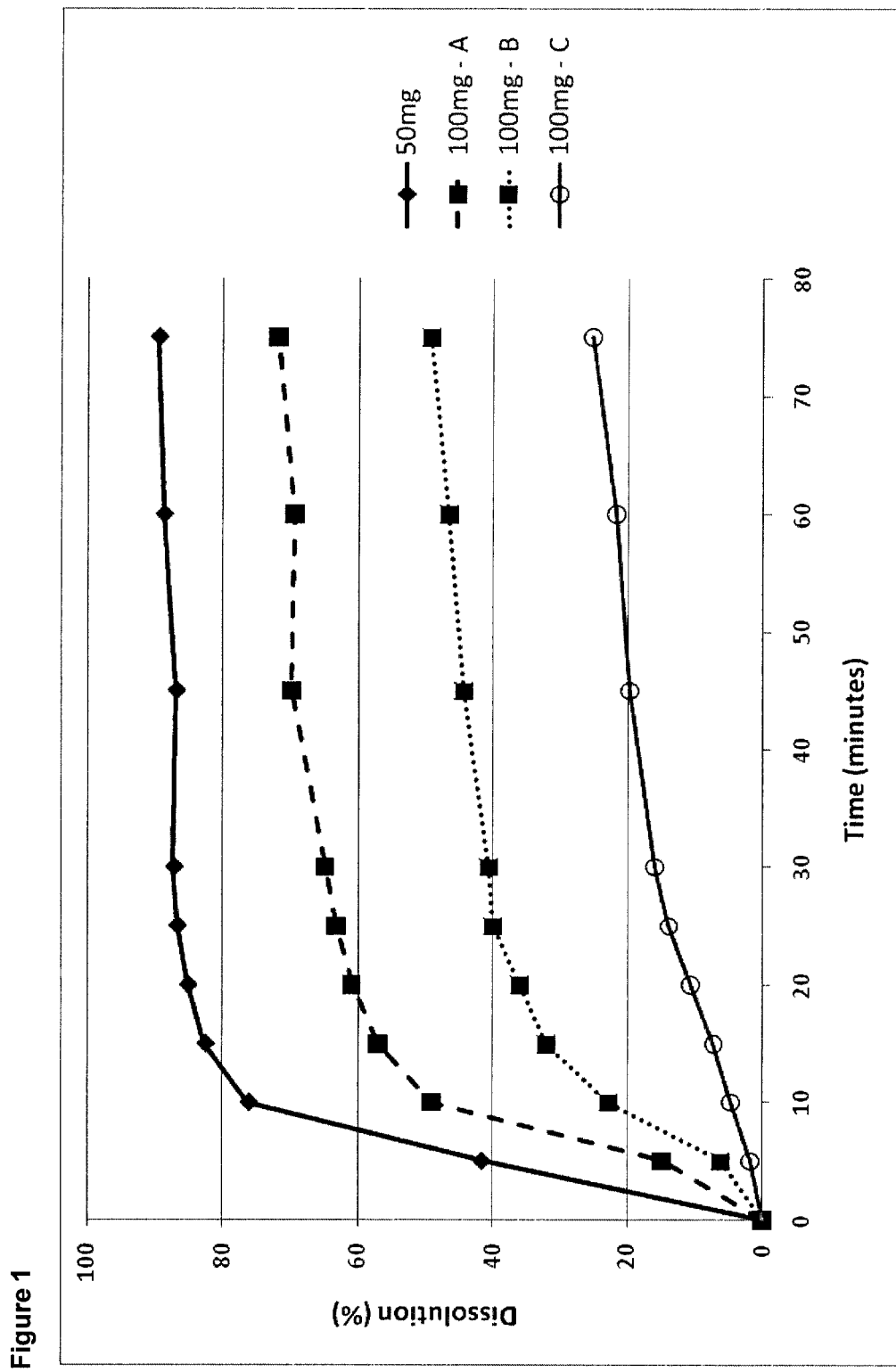
FIG. 1 shows a plot of the percent dissolution in 0.1N hydrochloric acid of existing tablets of strength 50 mg and 100 mg versus time.

The invention is further understood by reference to the following examples, which are intended to be purely exemplary of the invention. The present invention is not limited in scope by the exemplified aspects, which are intended as illustrations of single aspects of the invention only. Various modifications of the invention in addition to those described herein will become apparent to those skilled in the art from the foregoing description and accompanying figures. Such modifications fall within the scope of the appended claims.

In the examples below as well as throughout the application, the following abbreviations have the following meanings. If not defined, the terms have their generally accepted meanings.

GMP=good manufacturing practice
LOD=loss on drying
mg=milligram
MgSt=magnesium stearate
min=minute
mL=milliliter
nm=nanometer
JP=Japanese Pharmacopeia 15$^{th}$ Edition, English Version (Society of Japanese Pharmacopoeia) 2006
PhEur=European Pharmacopoeia 6$^{th}$ Edition (Directorate for the Quality of Medicines of the Council of Europe) 2009
PTFE=polytetrafluoroethylene
PVP=polyvinylpyrrolidone
rpm=revolutions per minute
SLS=sodium lauryl sulphate
SSG=sodium starch glycolate
USP—NF=United States Pharmacopeia 31/National Formulary 26 (The United States Pharmacopeia Convention) 2008
uv=ultraviolet
w/w=weight for weight Table 5 below shows materials used, pharmacopeial status, grade and supplier.

TABLE 5

| Material | Pharmacopeia | Grade | Supplier |
| --- | --- | --- | --- |
| Mannitol | PhEur | Pearlitol 160c | Roquette Freres |
|  | USP-NF | Pearlitol 120c | S.A. (France) |
|  | JP | Parteck M200 |  |
| Cellulose, | PhEur | Avicel ® PH-101 | FMC Biopolymer |
| microcrystalline | USP-NF | Avicel ® PH-102 | (Ireland) |
|  | JP |  |  |
| Sodium chloride | Ph Eur | Emprove | Merck Chemicals |
|  | BP |  | Ltd (UK) |
|  | JP |  |  |
|  | USP |  |  |
| di-Sodium | Ph Eur | Emprove | Merck Chemicals |
| hydrogen | BP |  | Ltd (UK) |
| phosphate | USP |  |  |
| Sodium | Ph Eur | Emprove | Merck Chemicals |
| hydrogen | BP |  | Ltd (UK) |
| carbonate | JP |  |  |
|  | USP |  |  |
| Sodium starch | Ph Eur | Glycolys LV | Roquette Freres |
| glycolate | USP-NF |  | S.A. (France) |
| Croscarmellose | Ph Eur | Ac-di-Sol | FMC Biopolymer |
| sodium | USP |  | (Ireland) |
|  | JP |  |  |

TABLE 5-continued

| Material | Pharmacopeia | Grade | Supplier |
|---|---|---|---|
| Magnesium stearate | Ph Eur USP-NF JP | NF Non Bovine | Mallinckrodt (USA) |
| Povidone | Ph Eur USP | Kollidon 30 K29/32 | BASF (Germany) ISP (Germany) |
| Sodium lauryl sulphate (Sodium dodecyl sulfate) | USP NF | N/A | Sigma Aldrich (UK) |
| Silified microcrystalline cellulose | Ph Eur JP NF | Prosolv 50 | JRS Pharma (Germany) |
| Pre-gelatinised starch 1500 | Ph Eur NF | Starch 1500 | Colorcon (USA) |
| Colloidal silica | USP-NF | Aeorsil | Evonik (Germany) |

Table 6 below shows equipment used, model and supplier.

TABLE 6

| Make | Model | Supplier |
|---|---|---|
| Diosna | P1/6 | Dierks & Söhne Gmbh, Osnabrück, Germany |
| Quadro | Comil U3 & Comil 194 | Quadro Engineering, Waterloo, Canada |
| WAB | Turbula T2F | Willy A. Bachofen AG, Muttenz, Switzerland |
| Riva | Piccola Nova | RivaSA, Buenos Aires, Argentina |
| Aeromatic | Strea 1 | Casburt Pharmaceutical Equipment, Stoke-on-Trent, UK |
| Alexanderwerk | WP 120 | Alexanderwerk AG, Remscheid, Germany |
| Copley Mobile Blender | Mobile Blender | Copley Scientific, Nottingham, UK |
| Niro-Fielder | PMA25 | Aeromatic Fielder, Eastleigh, UK |
| Fette | 1200 | Fette Compacting GmbH, Schwarzenbek, Germany |
| Aeromatic-Fielder | MP1 | Aeromatic Fielder, Eastleigh, UK |
| Vector | MFL.01 | Vector Corporation, Marion, IA, U.S.A |
| F3 | Manesty | Manesty, Knowsley, UK |

Example 1

Assessment of Dissolution Performance of Sixteen Alternative Tablet Forms

Sixteen different prototype tablets were prepared from a wet granulation formulation using methods well known to those skilled in the art. The composition of each of these tablets is set out in Table 3 above (not including water).

Formula (II) and the excipients described in Table 3 (total batch size approximately 250 g) are charged to a mixer-granulator (Diosna, 1 L) and mixed for 5 minutes at 300 rpm. Purified water (ranging from 15% w/w to 55% w/was set out in Table 3) is added to the powders with further mixing until a suitable wet mass is formed (ranging from 7 to 17 mins) at 300 rpm. The resultant granules are dried to appropriate moisture content (<6% LOD) using a fluid bed dryer (Vector) with an inlet air temperature of 60° C. The dried granules are milled using an appropriately sized screen (1 mm, Quadro Comil U3). Magnesium stearate is then added to the granules, which are then blended (WAB turbula) for 5 mins at 55 rpm before compressing into tablet cores using conventional tabletting equipment (F3 tablet press).

Figure 2:
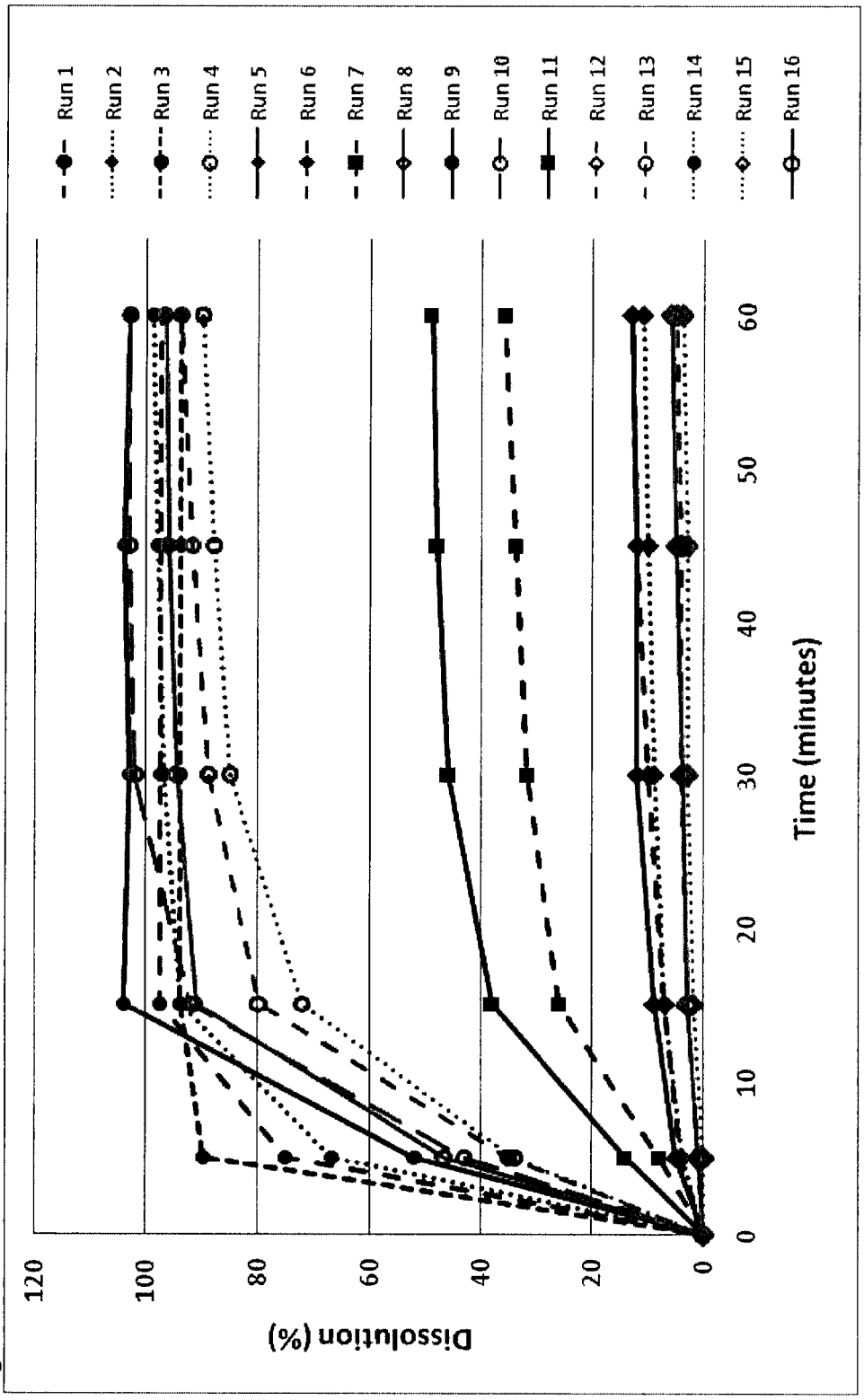
FIG. 2 shows a plot of the percent dissolution in 0.1N hydrochloric acid of sixteen alternative tablet forms versus time.

Dissolution was determined in accordance with the procedure outlined in the description above and the dissolution profiles are shown in FIG. 2.

Example 2

Assessment of Dissolution Performance of a Further Eight Alternative Tablet Forms A further eight different prototype tablets were prepared from a wet granulation formulation using methods well known to those skilled in the art. The composition of each of these tablets is set out in Table 4 above (not including water).

Formula (II) and the excipients described in Table 4 (total batch size approximately 600 g) are charged to a mixer-granulator (Diosna, 4 L) and mixed. Purified water (ranging from 15% w/w to 26.7% w/was set out in Table 4) is added to the powders with further mixing until a suitable wet mass is formed (ranging from 10 to 24 mins) at 200 rpm. The resultant granules are dried to appropriate moisture content (<5% LOD) using a fluid bed dryer (Aeromatic Strea) with an inlet air temperature of 100° C. The dried granules are milled using an appropriately sized screen (1 mm, Quadro Comil U3). Magnesium stearate is then added to the granules, which are then blended (WAB turbula) for 10 mins at 50 rpm before compressing into tablet cores using conventional tabletting equipment (Riva Piccola).

Figure 3:
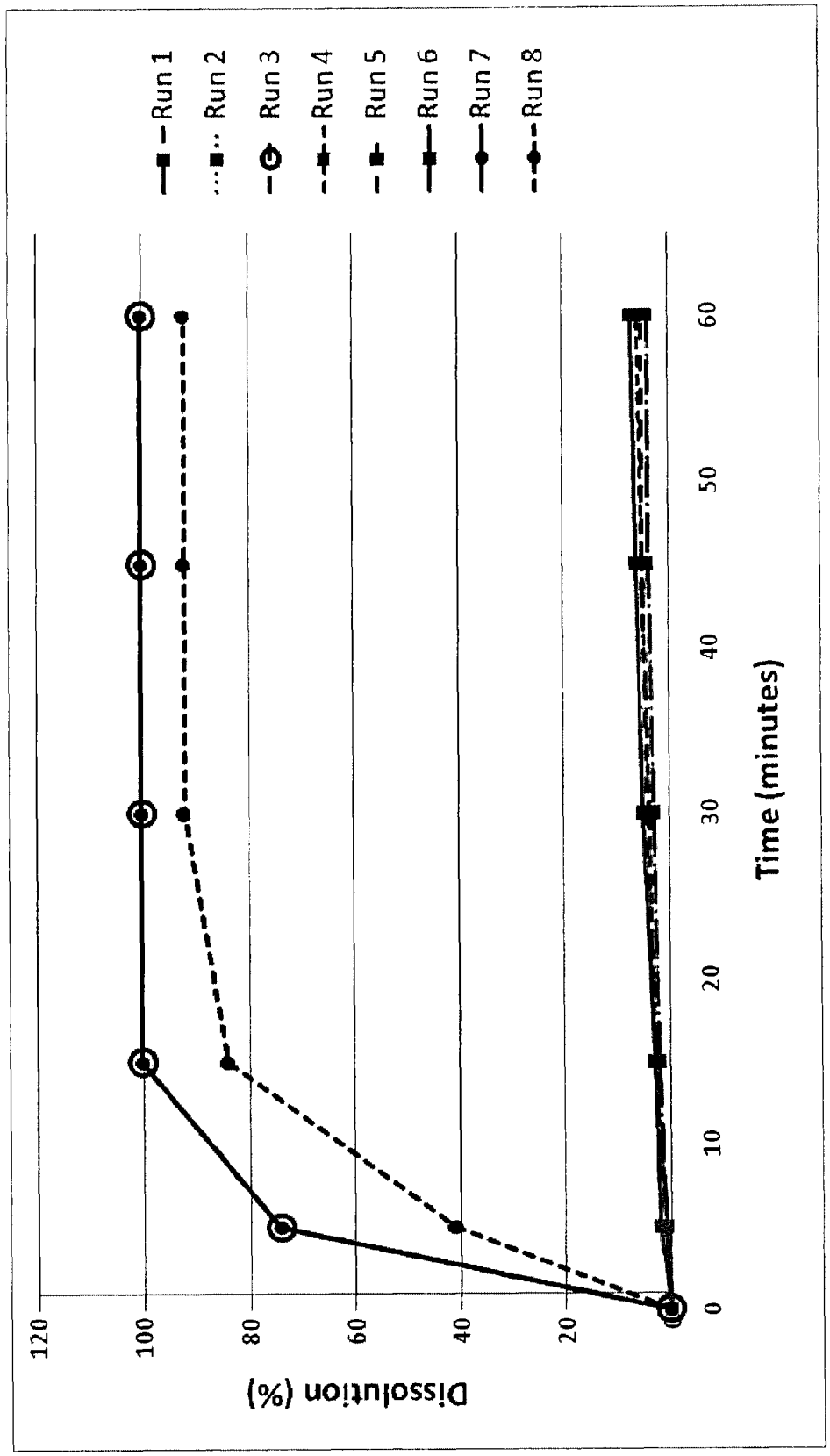
FIG. 3 shows a plot of the percent dissolution in 0.1N hydrochloric acid of a further eight alternative tablet forms versus time.

Dissolution was determined in accordance with the procedure outlined in the description above and the dissolution profiles are shown in FIG. 3.

Example 3

Assessment of Dissolution Performance of Tablets of Formula (II) Prepared by Roller Compaction Process Eight formulations selected from Examples 2 and 3 were assessed for feasibility in a roller compaction process using methods well known to those skilled in the art. The composition of each of these formulations is set out in Table 7 below. Formula (II) and the excipients described in Table 7 (total batch size approximately 1.5 kg) are charged to a mixer to produce a homogenous mix (Copley Mobile Blender) for 5 minutes at 30 rpm. The homogeneous mix is then passed through a roller compactor (Alexanderwerk, 40 mm roller size, 25 bar roller pressure, 2.5 rpm roller speed, 2.0 mm roller-gap size) to produce dry granules. The dry granules are then blended with magnesium stearate (Copley Mobile Blender). The resultant granules are compressed into tablet cores using conventional tabletting equipment (Riva Piccola).

TABLE 7

| Component | Formulation (% w/w) | | | | | | | |
|---|---|---|---|---|---|---|---|---|
| | 1 | 2 | 3 | 4 | 5 | 6 | 7 | 8 |
| Formula (II) | 37.9 | 25.2 | 37.9 | 37.9 | 37.9 | 37.9 | 37.9 | 37.9 |
| Mannitol | 22.1 | 54.8 | 27.1 | 27.1 | 45.1 | 45.1 | 42.1 | 45.1 |
| (Silicified) Microcrystalline cellulose | 0 | 0 | 15 | 15 | 10 | 10 | 10 | 10 |
| Sodium hydrogen carbonate | 30 | 10 | 10 | 10 | 0 | 0 | 0 | 0 |
| Povidone | 3 | 3 | 3 | 3 | 0 | 0 | 3 | 0 |
| Sodium Starch glycolate | 5 | 5 | 5 | 5 | 5 | 5 | 5 | 5 |
| Colloidal silica | 0.5 | 0.5 | 0.5 | 0.5 | 0.5 | 0.5 | 0.5 | 0.5 |
| Intragranular Magnesuim Stearate | 0.5 | 0.5 | 0.5 | 0.5 | 0.5 | 0.5 | 0.5 | 0.5 |

TABLE 7-continued

| | Formulation (% w/w) | | | | | | | |
|---|---|---|---|---|---|---|---|---|
| Component | 1 | 2 | 3 | 4 | 5 | 6 | 7 | 8 |
| Extragranular Magnesuim Stearate | 1 | 1 | 1 | 1 | 1 | 1 | 1 | 1 |

Formulations 1, 2, 3 and 8 were manufactured using Pearlitol 160 C. The remaining formulations used Parteck M200 mannitol. Formulations 3, 4, 6 and 7 used microcrystalline cellulose (Avicel PH101). Formulations 5 and 8 used silicified microcrystalline cellulose (Prosolv 50).

Figure 4:
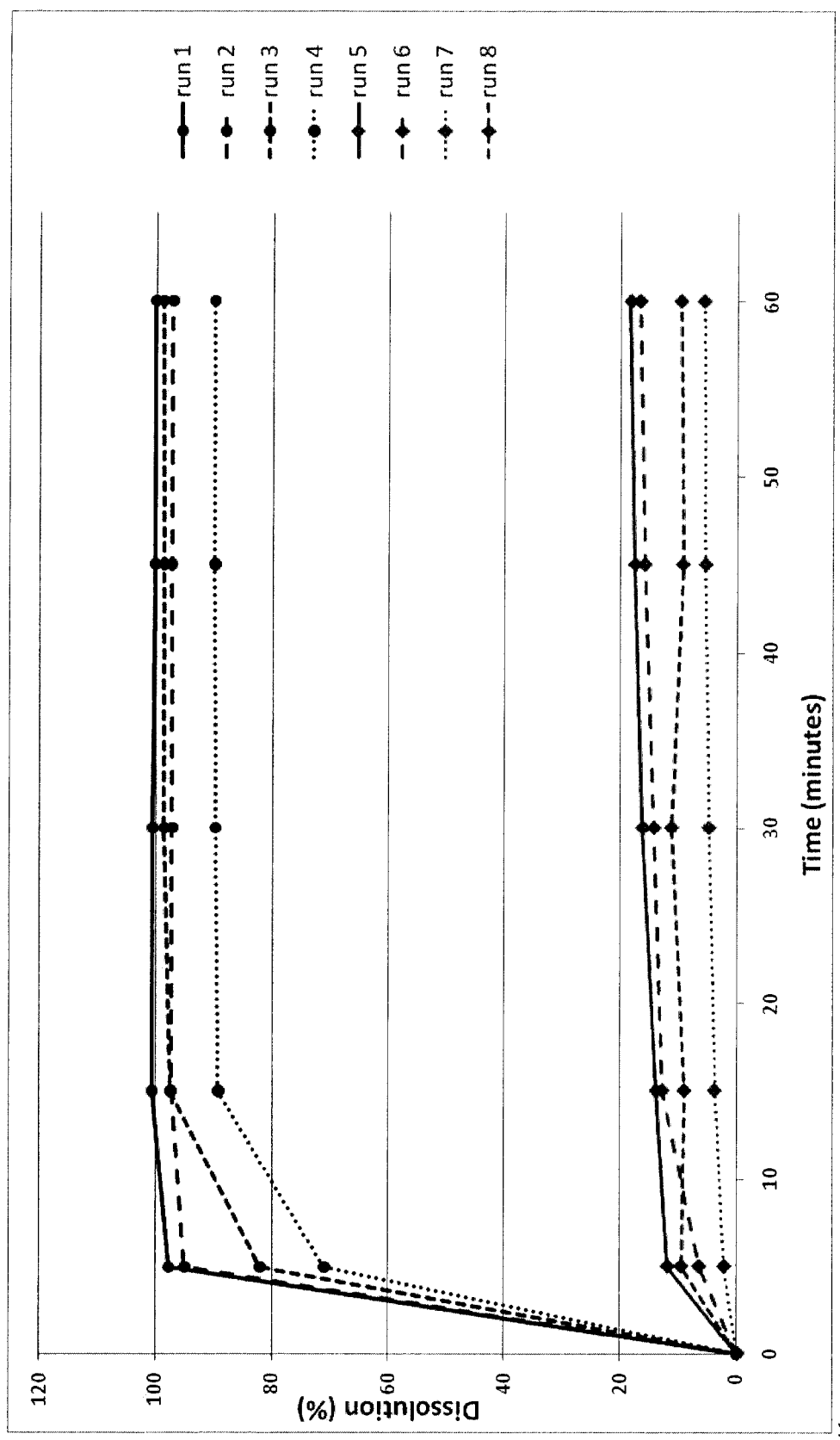
FIG. 4 shows a plot of the percent dissolution in 0.1N hydrochloric acid of eight tablet forms obtained via a roller compaction process versus time.

Dissolution was determined in accordance with the procedure outlined in the description above and the dissolution profiles are shown in FIG. 4.

Example 4

Assessment of Dissolution Performance of Tablets of Formula (II) Prepared by Direct Compression Tablets were prepared using direct compression formulation using methods well known to those skilled in the art. The composition of the tablets is as per Table 3, Run 9 above (without the addition of water).

Formula (II) and the excipients described in Table 3, Run 9 (total batch size approximately 250 g) are charged to a mixer-granulator (Diosna, 1 L) and mixed for 5 minutes at 300 rpm. Magnesium stearate is then added to the blend, which is then blended (WAB Turbula) for 5 minutes at 55 rpm before compressing into tablet cores using conventional tabletting equipment (F3 tablet press).

Figure 5:
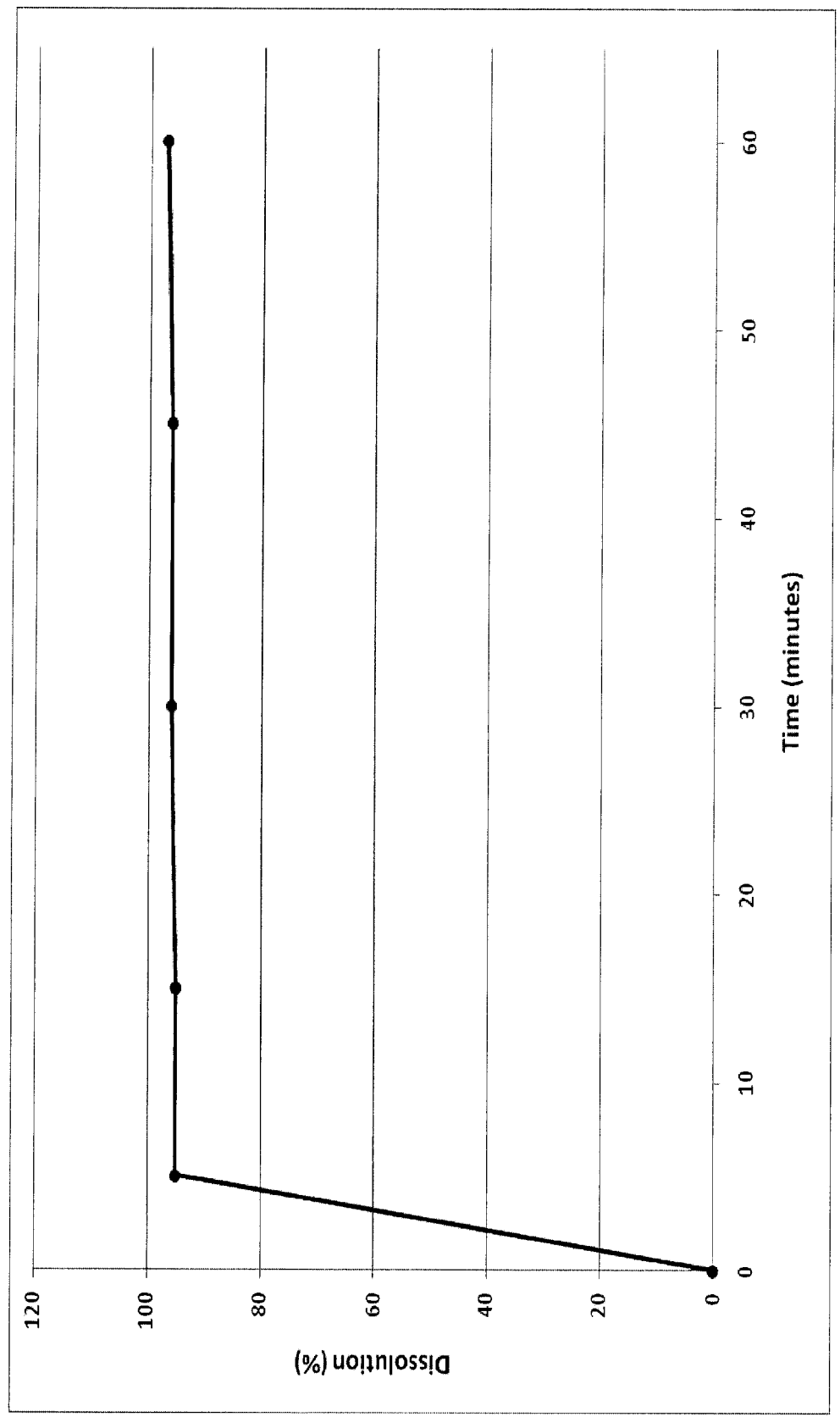
FIG. 5 shows a plot of the percent dissolution in 0.1N hydrochloric acid of a tablet form obtained via a direct compression process versus time.

Dissolution was determined in accordance with the procedure outlined in the description above and the dissolution profiles are shown in FIG. 5.

Example 5

Preparation of Tablets of Formula (II)

Tablets containing the components set out in Table 8 below were prepared using methods well known to those skilled in the art, in particular using conventional mixing, wet granulation, compression and film coating processes, according to GMP.

Formula (II), mannitol, sodium hydrogen carbonate, sodium starch glycolate and povidone are charged to a mixer-granulator (PMA25) and mixed. Purified water is added to the powders with further mixing until a suitable wet mass is formed. The wet mass may be passed through a screen to break up any large agglomerates. The resultant granules are dried to appropriate moisture content (<5% LOD) using a fluid bed dryer (MP1). The dried granules are milled using an appropriately sized screen (for example 1.1 mm, Comil 194). Magnesium stearate is then added to the granules, which are then blended (Copley) before compressing into tablet cores using conventional tabletting equipment (Fette 1200).

TABLE 8

| Tablet strength Components | 50 mg mg/tablet | 100 mg mg/tablet | 150 mg mg/tablet | Standard |
|---|---|---|---|---|
| Formula (II) | 63.1 | 126.2 | 189.3 | AstraZeneca |
| Mannitol | 61.8 | 248.6 | 185.3 | Ph Eur, NF, JP |

TABLE 8-continued

| Tablet strength Components | 50 mg mg/tablet | 100 mg mg/tablet | 150 mg mg/tablet | Standard |
|---|---|---|---|---|
| Sodium hydrogen carbonate | 25.0 | 75.0 | 74.9 | Ph Eur, USP, JP |
| Sodium starch glycolate | 8.3 | 25.0 | 25.0 | Ph Eur, NF |
| Povidone | 5.0 | 15.0 | 15.0 | Ph Eur, USP, JP, NF |
| Magnesium stearate | 3.3 | 10.0 | 10.0 | Ph Eur, NF |

Example 6

Assessment of Dissolution Performance of Additional Tablet Forms

Potassium hydrogen carbonate ($KHCO_3$), magnesium carbonate ($MgCO_3$) and sodium carbonate ($Na_2CO_3$) were incorporated into the tablet formulation in place of sodium hydrogen carbonate. The level of each was corrected to evolve the same quantity of carbon dioxide.

Sodium carbonate ($Na_2CO_3$) was incorporated at two concentrations to provide better understanding of the mechanism of action of these effervescent agents in the formulation. This took advantage of the fact that the reaction of sodium carbonate with hydrochloric acid takes place in two stages:

Stage I: sodium carbonate is converted to sodium hydrogen carbonate ($NaHCO_3$) as shown in the reaction:

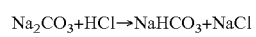

$$Na_2CO_3 + HCl \rightarrow NaHCO_3 + NaCl$$

Stage 11: the gas, carbon dioxide is released

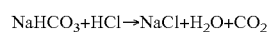

$$NaHCO_3 + HCl \rightarrow NaCl + H_2O + CO_2$$

Accordingly, sodium carbonate has stronger alkalizing activity compared to sodium hydrogen carbonate due to its capability to accept two hydrogen ions but has slower effervescent activity as evolution of the gas ($CO_2$) requires two steps reaction to take place.

Therefore, two levels of sodium carbonate were investigated. The lower level (9.5%) gave similar alkalisation capacity to 15% sodium hydrogen carbonate but with a lower amount of $CO_2$ to evolve in acidic environment. The higher level (15%) evolved the same total amount of $CO_2$ as 15% sodium hydrogen carbonate but at slower rate and with higher alkalisation capacity.

In addition, arginine and meglumine were investigated as alternatives to sodium hydrogen carbonate. Arginine and meglumine provide alkalising activity without any effervescent activity.

Moreover, citric acid was incorporated in one formulation to provide acidity to the microenvironment of the tablets and counteract the alkalising effect of sodium hydrogen carbonate. The level of citric acid was adjusted to neutralise the alkalinity of sodium hydrogen carbonate.

Furthermore, incorporation of higher levels of Formula (II) in the formulation was included at two levels of sodium hydrogen carbonate, 15% and 25%, to address possible correlation between the quantities of Formula (II) and the quantity of sodium hydrogen carbonate required to allow satisfactory dissolution.

Additionally, Polyplasdone® Crospovidone superdisintegrant was investigated in the formulation to replace sodium hydrogen carbonate and sodium starch glycolate in order to provide the possibility for rapid disintegration through a combination of swelling and wicking mechanism of disintegrations. Polyplasdone disintegrants are highly compressible materials and therefore higher level could be used to provide quicker disintegration. Polyplasdone® Crospovidone was investigated at two concentration 10% and 15%. Meglumine was included in these two formulations to provide high local pH (to prevent active pharmaceutical ingredient (API) gelling in acidic environment) and consequently offering a better opportunity to achieve complete dissolution in acid.

The formulation components and composition for each of the alternative tablet forms in Example 6 are presented in Tables 9, 10 and 11.

TABLE 9

| Component | Supplier/Trade name | Function |
| --- | --- | --- |
| Formula (II) | AstraZeneca/DSM Linz | Active Pharmaceutical Ingredient |
| Mannitol | Roquette Pearlitol 50C | Filler |
| sodium hydrogen carbonate (NaHCO3) | Merck Emprove | effervescent/ alkalizing agent |
| Potassium hydrogen carbonate (KHCO3) | Merck EMPROVE ® exp Ph Eur, BP, USP, FCC, E501 | effervescent/ alkalizing agent |
| magnesium carbonate (MgCO3) | Merck Emprove, Heavy | effervescent/ alkalizing agent |
| sodium carbonate (Na2CO3) | Merck EMPROVE ® exp Ph Eur, BP, NF, anhydrous | effervescent/ alkalizing agent |
| Citric Acid | Merck EMPROVE ® exp Ph Eur, BP, JP, USP, E 330, FCC, anhydrous | Acidifying agent |
| L-arginine (Arg) | Merck EMPROVE ® exp Ph Eur, USP | alkalizing agent |
| Meglumine (Megl) | Merck EMPROVE ® api Ph Eur, JP, USP | alkalizing agent |
| Crospovidone (CrosPosv) | Polyplasdone ® Crospovidone | Disintegrant |
| Sodium Starch Glycolate (SSG) | Expltab | Disintegrant |
| Polyvinylpyrrolidone (PVP) | BASF Kollidon K30 | Binder |
| Magnesium Stearate (MgSt) | Mallinkrodt non-bovine | Lubricant |

Batches of drug substance and excipients were dispensed to form a total nominal batch size of 600 g (Table 11). Magnesium stearate was included in the nominal total but was not included during granulation. Following drying, magnesium stearate was added to make up 2% of the total dry granules.

A wet granulation process was used to prepare the granules for tabletting using the method below.

Batches were dry blended for 4 min at 440 rpm with chopper speed of 1500 rpm using Diosna granulator P1/6 (Dierks & Söhne Gmbh, Osnabruck, Germany) in the 4 L bowl.

Water was added drop wise at a rate of 15 mL.min-1 to a total volume of 8-12% (w/w). The endpoint was checked by passing a sample of powder through a 1 mm sieve and judging whether there were fines and whether most of the materials were granular.

The wet mass was dried using Niro-Aeromatic Strea fluid bed dryer (Casburt Pharmaceutical Equipment, Stoke-on-Trent, UK) with a maximum inlet temperature of 90° C. and an appropriate fluidizing airflow. Extent of drying was determined using a moisture analyser (Mettler Toledo HB43) to <2%.

The dried granular mass was milled at 3000 rpm through a 1.0 mm screen using a U3 bench top Quadro Comil mill (Quadro Engineering, Waterloo, Canada).

The lubricant was then added at level of 2% by weight of the dried mass of granules and was blended using a Turbula blender (Willy A. Bachofen A G, Muttenz, Switzerland) at 50 rpm for 15 min.

The resultant mixtures were compressed using an F3 Manesty press (Casburt Pharmaceutical Equipment, Stoke-on-Trent, UK). The target compression force was 14 kN as used during A23 [RITA.000-376-136]. The compression force was assessed using DAAS instrumentation (Waltti Electronics Ltd., Kuopio, Finland).

Batches were compressed using 11 mm round concave tooling. Tablets were compressed to a target weight of 500 mg. Some tablets were collected from the line to allow weight and hardness to be correlated with compression force.

The resultant tablets were de-dusted and kept in air tight plastic bottles for analysis.

TABLE 10

| | Run | | | | | | | | | | | |
| --- | --- | --- | --- | --- | --- | --- | --- | --- | --- | --- | --- | --- |
| | 1 | 2 | 3 | 4 | 5 | 6 | 7 | 8 | 9 | 10 | 11a | 11b |
| Formula (II) (%) | 37.9 | 37.9 | 37.9 | 37.9 | 37.9 | 37.9 | 37.9 | 37.9 | 37.9 | 37.9 | 50 | 50 |
| NaHCO3 (%) | 15 | 0 | 0 | 15 | 0 | 0 | 0 | 0 | 0 | 0 | 15 | 25 |
| Na2CO3 (%) | 0 | 15 | 9.465 | 0 | 0 | 0 | 0 | 0 | 0 | 0 | 0 | 0 |
| Citric acid (%) | 0 | 0 | 0 | 34.305 | 0 | 0 | 0 | 0 | 0 | 0 | 0 | 0 |
| KHCO3 (%) | 0 | 0 | 0 | 0 | 17.88 | 0 | 0 | 0 | 0 | 0 | 0 | 0 |
| MgCO3 (%) | 0 | 0 | 0 | 0 | 0 | 15.06 | 0 | 0 | 0 | 0 | 0 | 0 |
| Arg (%) | 0 | 0 | 0 | 0 | 0 | 0 | 31.1 | 0 | 0 | 0 | 0 | 0 |
| Megl (%) | 0 | 0 | 0 | 0 | 0 | 0 | 0 | 34.86 | 34.86 | 34.86 | 0 | 0 |
| CrosPove (%) | 0 | 0 | 0 | 0 | 0 | 0 | 0 | 0 | 10 | 15 | 0 | 0 |
| SSG (%) | 5 | 5 | 5 | 5 | 5 | 5 | 5 | 5 | 0 | 0 | 5 | 5 |
| PVP (%) | 3 | 3 | 3 | 3 | 3 | 3 | 3 | 3 | 3 | 3 | 3 | 3 |
| MgSt (%) | 2 | 2 | 2 | 2 | 2 | 2 | 2 | 2 | 2 | 2 | 2 | 2 |
| Mannitol (%) | 37.1 | 37.1 | 42.64 | 2.795 | 34.22 | 37.04 | 20.99 | 17.24 | 12.24 | 7.24 | 25 | 15 |

TABLE 11

| | 1 | 2 | 3 | 4 | 5 | 6 | 7 | 8 | 9 | 10 | 11a | 11b |
|---|---|---|---|---|---|---|---|---|---|---|---|---|
| Formula (II) (g) | 227.4 | 227.4 | 227.4 | 227.4 | 227.4 | 227.4 | 227.4 | 227.4 | 227.4 | 227.4 | 300 | 300 |
| NaHCO3 (g) | 90 | 0 | 0 | 90 | 0 | 0 | 0 | 0 | 0 | 0 | 90 | 150 |
| Na2CO3 (g) | 0 | 90 | 56.79 | 0 | 0 | 0 | 0 | 0 | 0 | 0 | 0 | 0 |
| Citric acid (g) | 0 | 0 | 0 | 205.83 | 0 | 0 | 0 | 0 | 0 | 0 | 0 | 0 |
| KHCO3 (g) | 0 | 0 | 0 | 0 | 107.28 | 0 | 0 | 0 | 0 | 0 | 0 | 0 |
| MgCO3 (g) | 0 | 0 | 0 | 0 | 0 | 90.36 | 0 | 0 | 0 | 0 | 0 | 0 |
| Arg (g) | 0 | 0 | 0 | 0 | 0 | 0 | 186.66 | 0 | 0 | 0 | 0 | 0 |
| Megl (g) | 0 | 0 | 0 | 0 | 0 | 0 | 0 | 209.16 | 209.16 | 209.16 | 0 | 0 |
| CrosPove (g) | 0 | 0 | 0 | 0 | 0 | 0 | 0 | 0 | 60 | 90 | 0 | 0 |
| SSG (g) | 30 | 30 | 30 | 30 | 30 | 30 | 30 | 30 | 0 | 0 | 30 | 30 |
| PVP (g) | 18 | 18 | 18 | 18 | 18 | 18 | 18 | 18 | 18 | 18 | 18 | 18 |
| MgSt (g) | 12 | 12 | 12 | 12 | 12 | 12 | 12 | 12 | 12 | 12 | 12 | 12 |
| Mannitol (g) | 222.6 | 222.6 | 255.8 | 16.77 | 205.3 | 222.2 | 125.9 | 103.4 | 73.44 | 43.44 | 150 | 90 |

Disintegration time was measured using an Erweka Copley ZT74 disintegration machine. The experiment was carried out at 36-38° C. using 0.7 L tap water and the disc method. Six tablets were tested for each batch. Results are presented as mean±SD (n=6).

Sotax HT100 was used to determine the weight, hardness, thickness and diameter of 15 tablets from each batch. The Sotax is an automated tablet tester, which measures each parameter at a different station for a specified number of tablets using a specific method ("11 mm 500 mg Round Uncoated n15"). First the weight is measured, then the tablet is passed to a thickness gauge before being passed to a jaw where the diameter and hardness are measured. A report is then generated with individual data for each of the tablets tested, as well as the calculated mean and RSD for each batch. Results are presented as mean±SD (n=15).

The true density of the tablets was obtained by helium pycnometry using the AccuPyc. Ten tablets were weighed accurately, placed in the sample cup previously used for calibration and analysed. True density was calculated for each batch using the equation set out below and was found to be between 1.55 and 1.56 g/cc for each of them.

True density=(mass/volume of solids)

Tablet envelope density (apparent density) was then obtained by a volume displacement method using the GeoPyc. The same ten tablets were then placed in the 25.4 cm cylinder with DryFlo. The porosity was calculated by the GeoPyc using the true density data from above and the following equation:

Apparent density=(mass of tablets/envelope volume of tablets)

The porosity of the tablets was then determined using the apparent density and true density calculated above in the following equation:

Porosity=100×1−(apparent density/true density)

Dissolution was determined in accordance with the procedure outlined in the description above.

The amount of gas evolved as a result of the tablets being placed in an acidic environment was assessed. A 250 ml beaker filled with 100 ml of 0.1 N HCl (pH 1) was placed over a balance connected to a PC to transmit the weight at regular time interval (every 15 seconds). The balance was left to settle until the balance reading was stable. One tablet was dropped in the beaker and weight recording was started. The weight difference was calculated and plotted as a function of time.

Weight, hardness, disintegration time and porosity data are summarised in Table 12.

TABLE 12

| | Weight (mg) | | Hardness (kp) | | Disintegration time (s) | | Porosity (%) | |
|---|---|---|---|---|---|---|---|---|
| | Average | SD | Average | SD | Average | SD | Average | SD |
| 1 | 500.3 | 5.00 | 9 | 0.9 | 327.5 | 25.03 | 13.10 | 0.39 |
| 2 | 501.6 | 10.43 | 9 | 2.4 | 475.5 | 43.72 | 15.43 | 0.37 |
| 3 | 476.3 | 15.86 | 7 | 2.7 | 426.16 | 39.42 | 13.90 | 0.23 |
| 5 | 505.4 | 3.08 | 9 | 0.7 | 454 | 23.41 | 12.66 | 0.33 |
| 6 | 487.2 | 13.03 | 10 | 2 | 134 | 9.01 | 15.99 | 0.06 |
| 7 | 493 | 19.53 | 8 | 2.7 | 338 | 10.12 | 14.62 | 0.29 |
| 8 | 491.1 | 26.68 | 11 | 3.1 | 360.0 | 26.50 | 10.33 | 0.10 |
| 9 | 509.2 | 6.17 | 15 | 1.7 | 367.0 | 97.6 | 9.18 | 0.14 |
| 10 | 499.1 | 7.72 | 9 | 1.1 | 516.7 | 15.2 | 14.66 | 0.14 |
| 11a | 504.4 | 12.29 | 9 | 2.2 | 461.3 | 19.2 | 14.19 | 0.05 |
| 11b | 499.4 | 16.9 | 9 | 2 | 487.2 | 56.4 | 12.66 | 0.17 |

Figure 6:
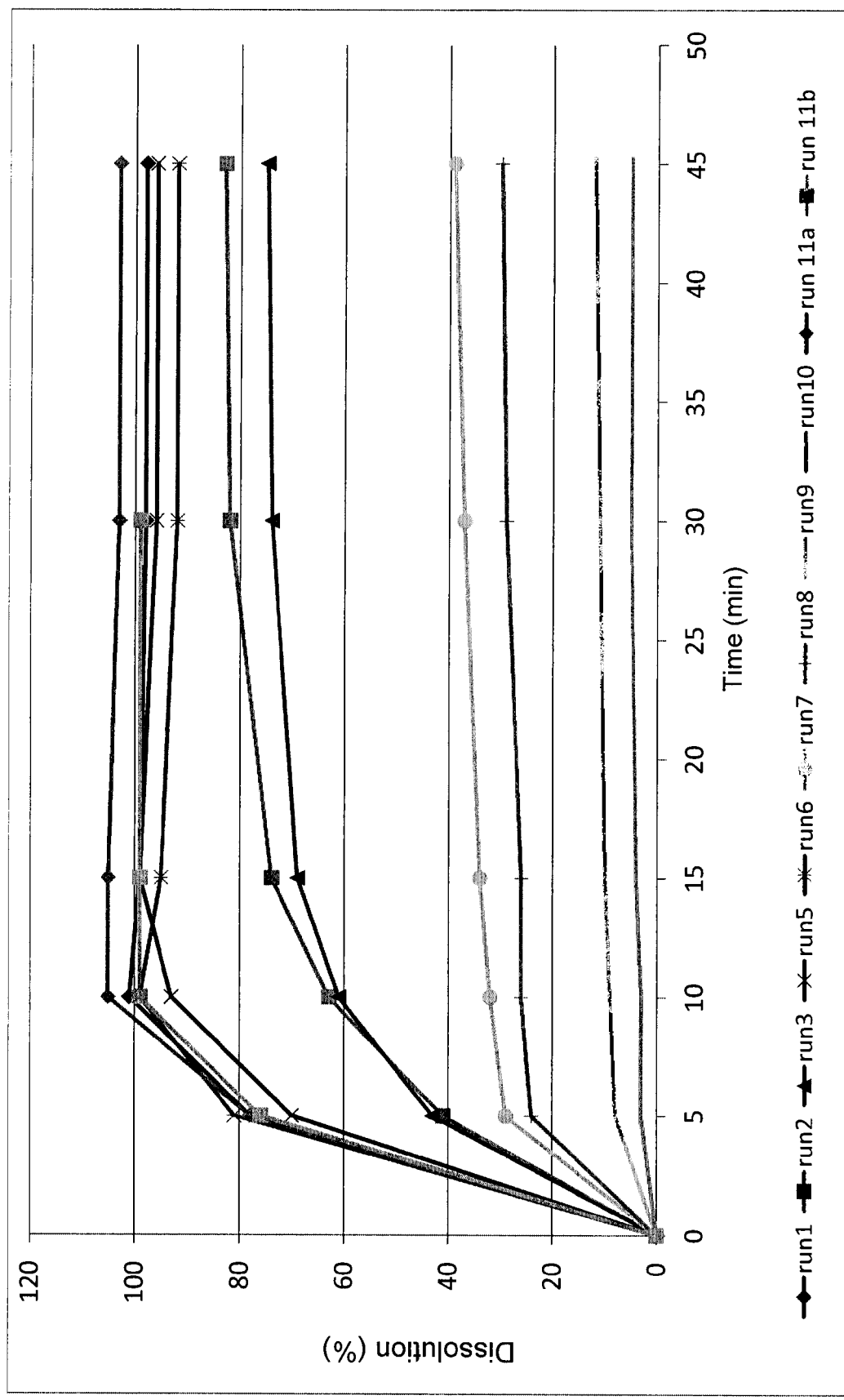
FIG. 6 shows a plot of the percent dissolution in 0.1N hydrochloric acid of a further twelve alternative tablet forms versus time.

The dissolution profiles of the tablets in 0.1 M HCl are presented in FIG. 6. No result is given for Run 4 as no satisfactory formulation could be achieved and therefore no dissolution measurement was taken.

Figure 7:
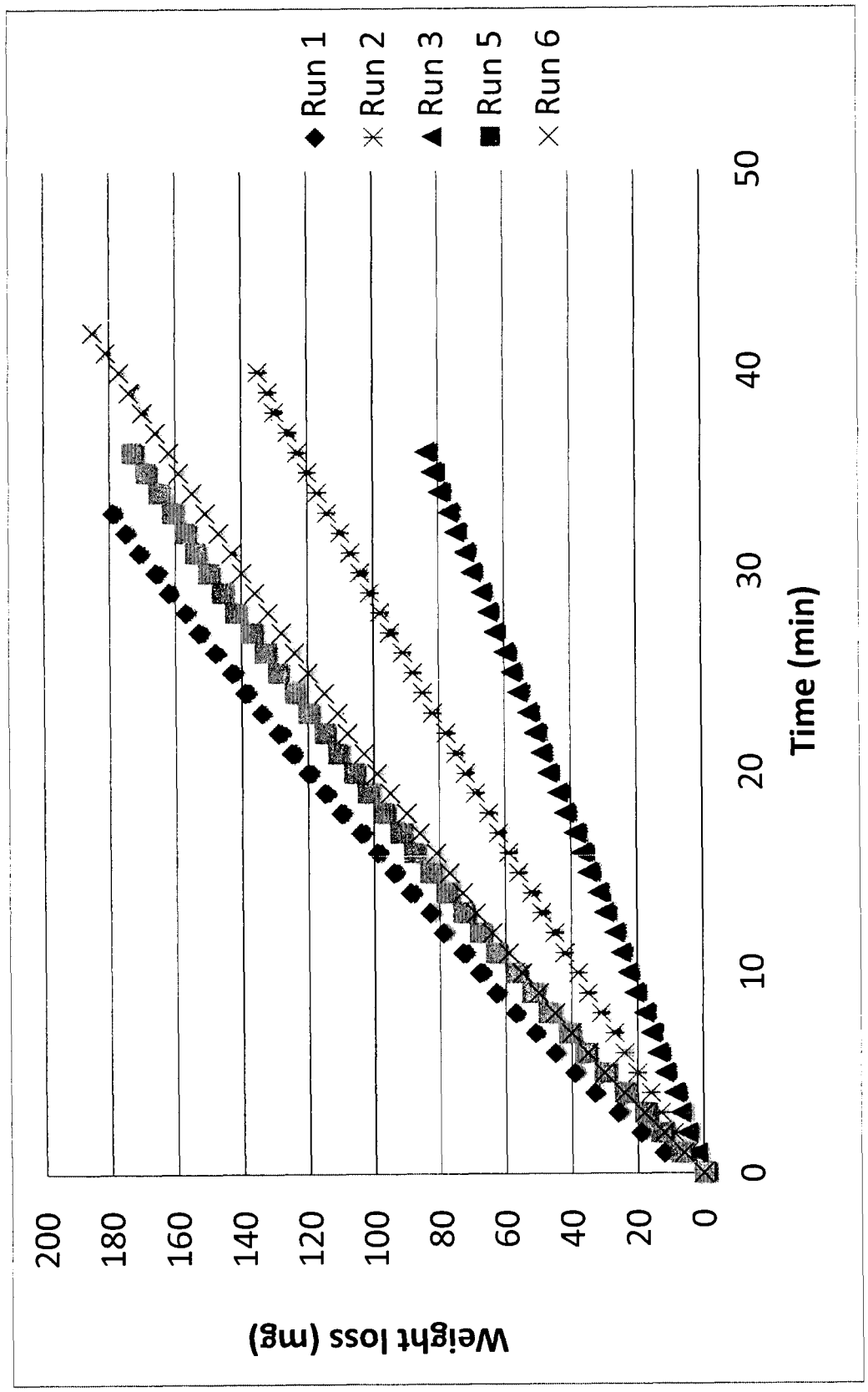
FIG. 7 shows a plot of weight loss versus time of five tablet forms after placing the tablets in 0.1 N HCl (run 1).
Figure 8:
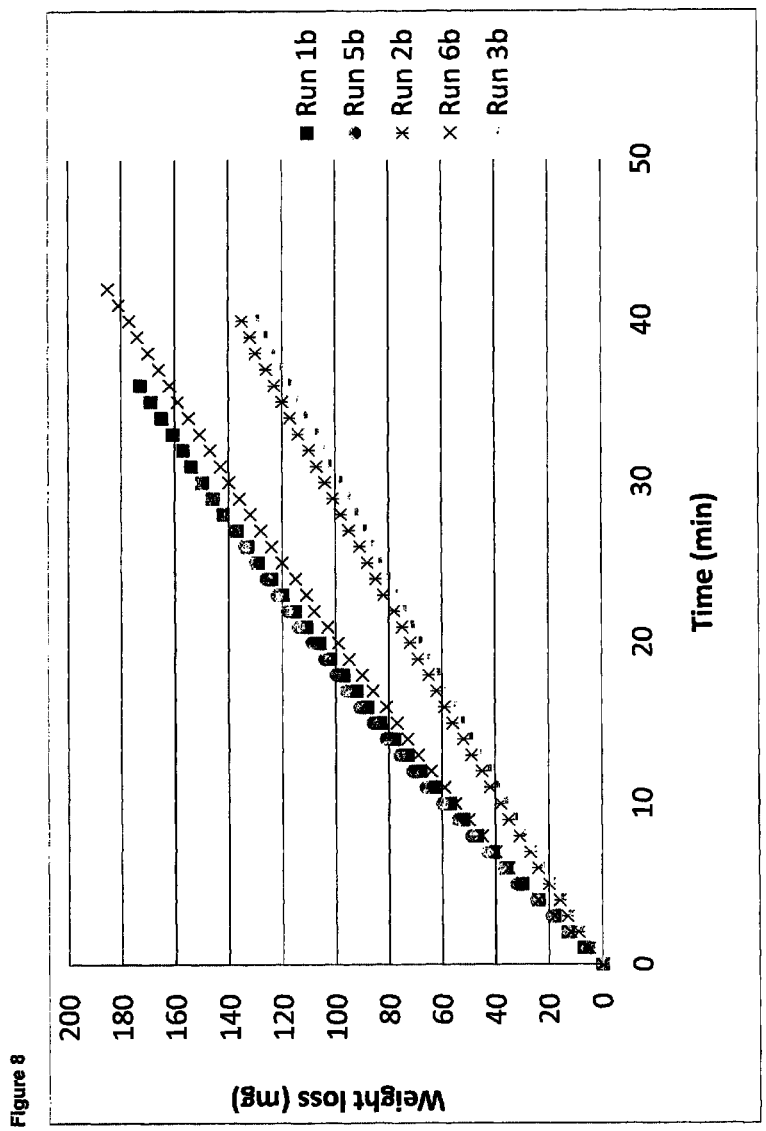
FIG. 8 shows a plot of weight loss versus time of five tablet forms after placing the tablets in 0.1 N HCl (run 2).
Figure 9:
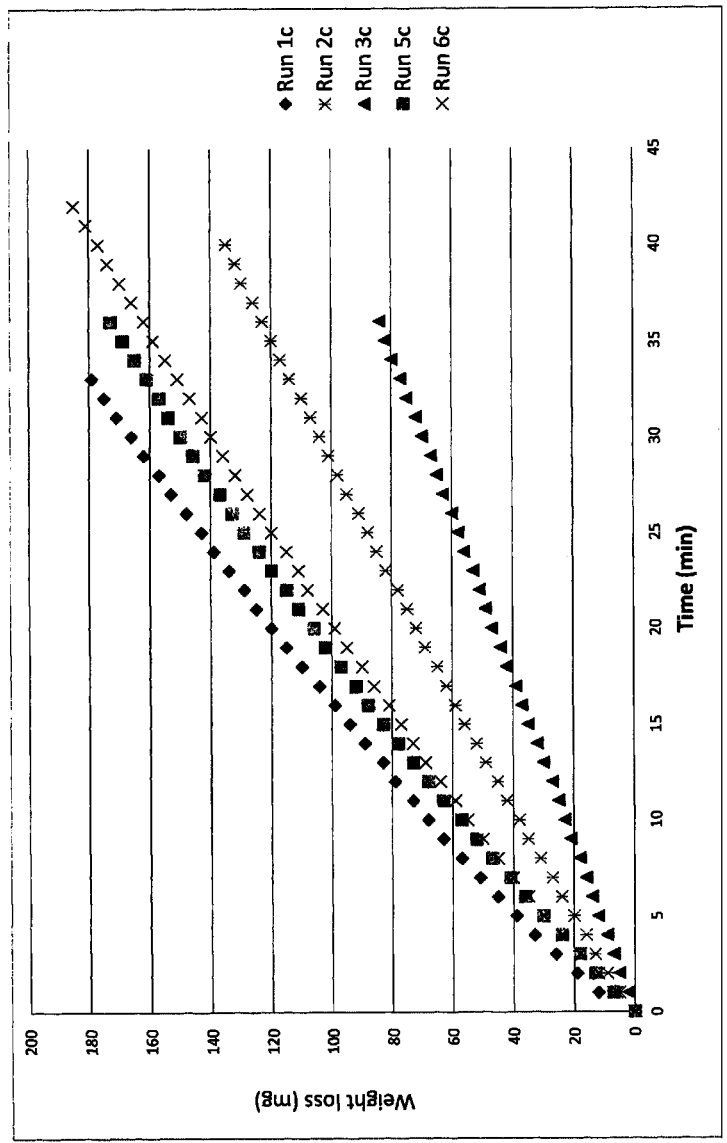
FIG. 9 shows a plot of weight loss versus time of five tablet forms after placing the tablets in 0.1 N HCl (run 3).

Results from gas evolution quantification are presented in FIGS. 7, 8 and 9.

The results showed that alkalising agents which did not additionally provide effervescent activity failed to provide tablets of Formula (II) which gave satisfactory dissolution. The results suggest that effervescent agents such as sodium hydrogen carbonate, potassium hydrogen carbonate and magnesium carbonate enhance the dissolution of the tablet.

The tablet with a lower level of sodium carbonate provided a lower level of dissolution compared to the tablet with a higher level of sodium carbonate. Furthermore, the tablet with the higher level of sodium carbonate provided dissolution at a lower rate and extent compared to tablets with sodium hydrogen carbonate. This could be explained as a result of slower carbon dioxide evolution.

Accordingly, the rate and extent of carbon dioxide evolution appear to effect the dissolution profile of the tablet.

The results further show that increased drug loading (for example greater than or equal to 50% w/w of Formula (II)) exhibiting a satisfactory dissolution profile can be achieved using sodium hydrogen carbonate. Furthermore, the results show that higher levels of sodium hydrogen carbonate (greater than or equal to 25%) were not necessary to achieve a satisfactory dissolution profile.

The invention claimed is:

1. A solid pharmaceutical composition comprising greater than 15% w/w of the compound of Formula (I):

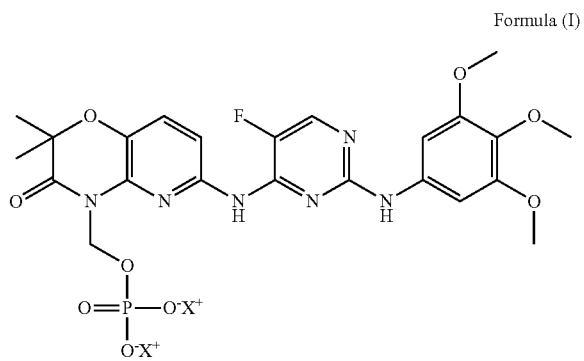

Formula (I)

wherein each X⁺ represents a monovalent cation;
and/or a hydrate thereof;
and an amount of one or more effervescent agents that is sufficient to provide satisfactory in vitro dissolution at low pH;
and further comprising one or more pharmaceutically acceptable ingredients.

2. The solid pharmaceutical composition according to claim 1 comprising greater than or equal to 25% w/w of the compound of Formula (I) and/or hydrate thereof.

3. The solid pharmaceutical composition according to claim 1 comprising less than or equal to 20% w/w of the effervescent agent.

4. The solid pharmaceutical composition according to claim 1 wherein the effervescent agent is sodium hydrogen carbonate.

5. The solid pharmaceutical composition according to claim 1 wherein each X⁺ in the compound of Formula (I) represents a sodium cation (Na⁺).

6. The solid pharmaceutical composition according to claim 1 wherein the compound of Formula (I) is in the form of an hexahydrate.

7. The solid pharmaceutical composition according to claim 1 wherein the compound of Formula (I) is in the form of Formula (II):

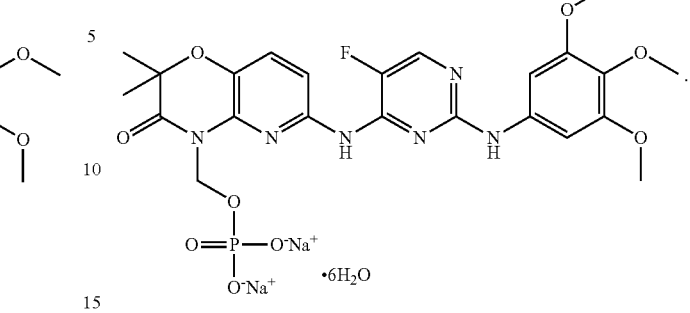

Formula (II)

8. A unit dosage form comprising greater than or equal to 60 mg of the compound of Formula (I):

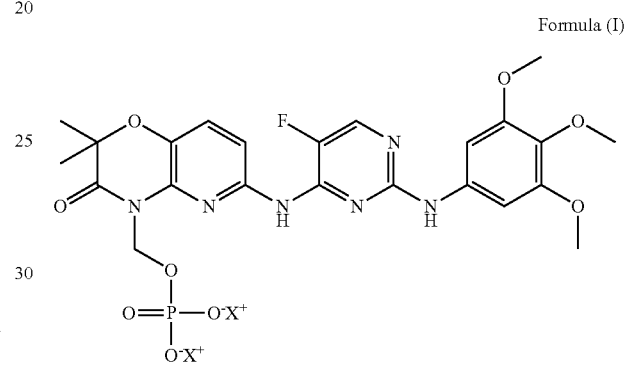

Formula (I)

wherein each X⁺ represents a monovalent cation; and/or a hydrate thereof;
and less than or equal to 110 mg of one or more effervescent agents that is sufficient to provide satisfactory in vitro dissolution at low pH;
and further comprising one or more pharmaceutically acceptable ingredients.

* * * * *